US008632824B2

(12) United States Patent
Purcell

(10) Patent No.: US 8,632,824 B2
(45) Date of Patent: Jan. 21, 2014

(54) PROCESS OF OBTAINING THYLAKOIDS FROM PHOTOSYNTHETIC ORGANISMS; PLANT FRACTIONS OBTAINED FROM THE PROCESS; PURE THYLAKOIDS; AND METHODS OF USE OF THYLAKOIDS AS ROS SCAVENGERS, PHOTO-PROTECTORS, BIOSENSORS, BIOFILTERS AND BIOREACTORS

(75) Inventor: Marc Purcell, Saint-Augustin-de-Desmaures (CA)

(73) Assignee: Purgenesis Technologies, Inc. (CA)

( * ) Notice: Subject to any disclaimer, the term of this patent is extended or adjusted under 35 U.S.C. 154(b) by 1590 days.

(21) Appl. No.: 11/734,449

(22) Filed: Apr. 12, 2007

(65) Prior Publication Data

US 2007/0202198 A1 Aug. 30, 2007

Related U.S. Application Data

(62) Division of application No. 10/169,931, filed as application No. PCT/CA00/01541 on Dec. 29, 2000, now Pat. No. 7,270,839.

(51) Int. Cl.
*A61K 36/00* (2006.01)

(52) U.S. Cl.
USPC .......................................... 424/725

(58) Field of Classification Search
None
See application file for complete search history.

(56) References Cited

U.S. PATENT DOCUMENTS 5,290,765 A * 3/1994 Wettlaufer et al. ............. 514/23
7,270,839 B2 * 9/2007 Purcell .......................... 424/774

FOREIGN PATENT DOCUMENTS

WO WO 97/40838 11/2007

OTHER PUBLICATIONS

Thylakoid Membrane Polypeptides of *Chlamydomonas reinhardtii*; Proc. Nat. Acad. Sci. USA; vol. 72, No. 6, pp. 2175-2179, Jun. 1975.
Canadian Office Action in Canadian Patent Application No. 2,393,816, Oct. 7, 2010, 3 pages, CIPO, Canada.

* cited by examiner

*Primary Examiner* — Terry A McKelvey
*Assistant Examiner* — Randall Winston
(74) *Attorney, Agent, or Firm* — Roylance Abrams Berdo & Goodman, L.L.P.; Alan L. Cantor

(57) ABSTRACT

This invention relates to a process by which an extract comprising integral thylakoids is obtained. The resulting extract is a potent dynamic antioxidant useful as a ROS (reactive oxygen species) scavenger. This extract is intended to be used for the treatment or prevention of diseases involving the generation of ROS, such as inflammatory diseases or cancer. This extract also finds a use as a solar screen because of its capacity to capture UV radiations and to dissipate the solar energy into heat.

18 Claims, 13 Drawing Sheets

A. lipid oxidation without antioxidant

B. lipid oxidation in the presence of an antioxidant which "allows" some lipid oxidation C. lipid oxidation in the presence of an efficient radical chain breaking antioxidant (such as Vitamin E)

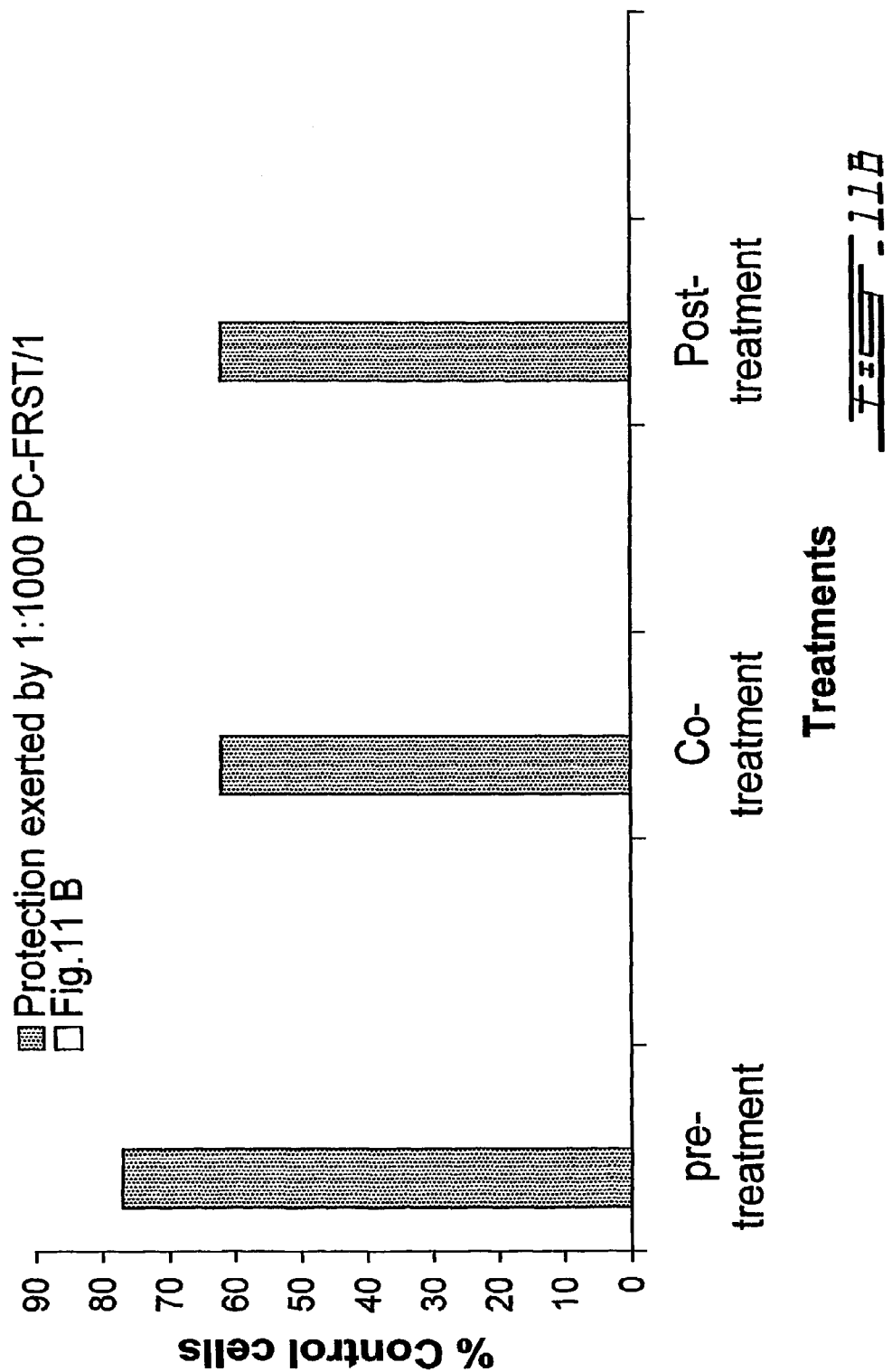

US 8,632,824 B2

PROCESS OF OBTAINING THYLAKOIDS FROM PHOTOSYNTHETIC ORGANISMS; PLANT FRACTIONS OBTAINED FROM THE PROCESS; PURE THYLAKOIDS; AND METHODS OF USE OF THYLAKOIDS AS ROS SCAVENGERS, PHOTO-PROTECTORS, BIOSENSORS, BIOFILTERS AND BIOREACTORS

CROSS-REFERENCE TO RELATED APPLICATIONS

This application is a divisional of U.S. patent application Ser. No. 10/169,931, filed Nov. 25, 2002, now U.S. Pat. No. 7,270,839, which is the 371 National Phase of International Application No. PCT/CA00/01541 filed on Dec. 29, 2000, which was published in English under PCT Article 21(2) as International Publication No. WO 01/49305, and which claims priority from Canadian patent application Serial No. 2,293,852 filed on Dec. 30, 1999. All of these applications are incorporated herein by reference in their entirety.

FIELD OF THE INVENTION

This invention relates to the isolation and recovery of thylakoids, which are present substantially in their integral and natural state, at least a portion of which is functional or activable. This invention also relates to the obtention of other soluble and insoluble plant fractions obtained upon the isolation of thylakoids. This invention further relates to the use of thylakoids as ROS scavengers, as photoprotectors, particularly against U.V. radiations, as well as biosensors, biofilters or bioreactors.

BACKGROUND OF THE INVENTION

Antioxidants have become increasingly popular, namely in the biomedical field, because of their capacity to prevent the formation and the noxious activity of reactive oxygen species (ROS).

Plants and other photosynthetic organisms are particularly well adapted to resist the effect of ROS, especially to protect vital organelle photosynthetic membranes called thylakoids against oxidative damages and the noxious action of U.V. radiations.

Sunlight plays a much larger role in our sustenance than we may expect: all the food we eat and all the fossil fuel we use is a product of photosynthesis, which is the process that converts energy in sunlight to chemical forms of energy that can be used by biological systems. Photosynthesis is carried out by many different organisms, ranging from plants to bacteria. The best known form of photosynthesis is the one carried out by higher plants and algae, as well as by cyanobacteria and their relatives, which are responsible for a major part of photosynthesis in oceans. All these organisms convert $CO_2$ (carbon dioxide) to organic material by reducing this gas to carbohydrates in a rather complex set of reactions. Electrons for this reduction reaction ultimately come from water, which is then converted to oxygen and protons. Energy for this process is provided by light, which is absorbed by pigments (primarily chlorophylls and carotenoids). Chlorophylls absorb blue and red light and carotenoids absorb blue-green light, but green and yellow light are not effectively absorbed by photosynthetic pigments in plants; therefore, light of these colors is either reflected by leaves or passes through the leaves.

Other photosynthetic organisms, such as cyanobacteria (formerly known as blue-green algae) and red algae, have additional pigments called phycobilins that are red or blue and that absorb the colors of visible light that are not effectively absorbed by chlorophyll and carotenoids. Yet other organisms, such as the purple and green bacteria (which, by the way, look fairly brown under many growth conditions), contain bacteriochlorophyll that absorbs in the infrared, in addition to in the blue part of the spectrum. These bacteria do not evolve oxygen, but perform photosynthesis under anaerobic (oxygen-less) conditions. These bacteria efficiently use infrared light for photosynthesis. Infrared is light with wavelengths above 700 nm that cannot be seen by the human eye; some bacterial species can use infrared light with wavelengths of up to 1000 nm. However, most pigments are not very effective in absorbing ultraviolet light (<400 nm), which also cannot be seen by the human eye. Light with wavelengths below 330 nm becomes increasingly damaging to cells, but virtually all light at these short wavelengths is filtered out by the atmosphere (most prominently the ozone layer) before reaching the earth. Even though most plants are capable of producing compounds that absorb ultraviolet light, an increased exposure to light around 300 nm has detrimental effects on plant productivity.

Photosynthetic pigments come in a huge variety: there are many different types of (bacterio)chlorophyll, carotenoids, and phycobilins, differing from each other in their precise chemical structure. Pigments generally are bound to proteins, which provide the pigment molecules with the appropriate orientation and positioning with respect to each other Light energy is absorbed by individual pigments, but is not used immediately by these pigments for energy conversion. Instead, the light energy is transferred to chlorophylls that are in a special protein environment where the actual energy conversion event occurs: the light energy is used to transfer an electron to a neighboring pigment. Pigments and protein involved with this actual primary electron transfer event together are called the reaction center. A large number of pigment molecules (100-5000), collectively referred to as antenna, "harvest" light, capture photons, and transfer the light energy to the same reaction center. The purpose is to maintain a high rate of electron transfer in the reaction center, even at lower light intensities. The denomination P680 is assigned to the chlorophyll pigments of the reaction center PSII, because the pair of chlorophylls entering it composition absorbs light mostly at a 680 nm wavelength.

Many antenna pigments transfer their light energy to a single reaction center by having this energy transfer to another antenna pigment, and yet to another, etc., until the energy is "trapped" in the reaction center. Each step of this energy transfer must be very efficient to avoid a large loss in the overall transfer process, and the association of the various pigments with proteins ensures that transfer efficiencies are high by having appropriate pigments close to each other, and by having an appropriate molecular geometry of the pigments with respect to each other. An exception to the rule of protein-bound pigments are green bacteria with very large antenna systems: a large part of these antenna systems consists of a "bag" (named chlorosome) of up to several thousand bacteriochlorophyll molecules that interact with each other and that are not in direct contact with protein. Chlorophyll is used by all photosynthetic organisms as the link between excitation energy transfer and electron transfer. Of particular note is the rate with which these transfer reactions need to occur. As the lifetime of the excited state is only several nanoseconds (1 nanosecond (ns) is $10^{-9}$ s), after absorption of a quantum, energy transfer and charge separation in the reaction center must have occurred within this time period. Energy transfer rates between pigments are very rapid, and charge separation in reaction centers occurs in 3-30 picoseconds (1 picosecond (ps) is $10^{-12}$ s). Subsequent electron transfer steps are significantly slower (200 ps-20 ms) but, nonetheless, the electron transport chain is sufficiently fast that at least a significant part of the absorbed sunlight can be used for photosynthesis. The pigments have a specific organisation which should be preserved upon isolation and purification of thylakoids if the maintenance of the function of the latter is sought.

In many systems the size of the photosynthetic antenna is flexible, and photosynthetic organisms growing at low light (in the shade, for example) generally will have a larger number of antenna pigments per reaction center than those growing at higher light intensity. However, at high light intensities (for example, in full sunlight) the amount of light that is absorbed by plants exceeds the capacity of electron transfer initiated by reaction centers. Plants have developed means to convert some of the absorbed light energy to heat rather than to use the absorbed light necessarily for photosynthesis. However, in particular the first part of photosynthetic electron transfer in plants is rather sensitive to overly high rates of electron transfer, and part of the photosynthetic electron transport chain may be shut down when the light intensity is too high; this phenomenon is known as photoinhibition.

The initial electron transfer (charge separation) reaction in the photosynthetic reaction center sets into motion a long series of redox (reduction-oxidation) reactions, passing the electron along a chain of cofactors and filling up the "electron hole" on the chlorophyll, much like in a bucket brigade. All photosynthetic organisms that produce oxygen have two types of reaction centers, named photosystem II and photosystem I (PS II and PS I, for short), both of which are pigment/protein complexes that are located in specialized membranes called thylakoids. In eukaryotes (plants and algae), these thylakoids are located in chloroplasts (organelles in plant cells) and often are found in membrane stacks (grana). Prokaryotes (bacteria) do not have chloroplasts or other organelles, and photosynthetic pigment-protein complexes either are in the membrane around the cytoplasm or in invaginations thereof (as is found, for example, in purple bacteria), or are in thylakoid membranes that form much more complex structures within the cell (as is the case for most cyanobacteria).

All the chlorophyll in oxygenic organisms is located in thylakoids, and is associated with PS II, PS I, or with antenna proteins feeding energy into these photosystems. PS II is the complex where water splitting and oxygen evolution occurs. Upon oxidation of the reaction center chlorophyll in PS II, an electron is pulled from a nearby amino acid (tyrosine) which is part of the surrounding protein, which in turn gets an electron from the water-splitting complex. From the PS II reaction center, electrons flow to free electron carrying molecules (plastoquinone) in the thylakoid membrane, and from there to another membrane-protein complex, the cytochrome $b_6f$ complex. The other photosystem, PS I, also catalyzes light-induced charge separation in a fashion basically similar to PS II: light is harvested by an antenna, and light energy is transferred to a reaction center chlorophyll, where light-induced charge separation is initiated. However, in PS I electrons are transferred eventually to NADP (nicotinamide adenosine dinucleotide phosphate), the reduced form of which can be used for carbon fixation. The oxidized reaction center chlorophyll eventually receives another electron from the cytochrome $b_6f$ complex. Therefore, electron transfer through PS II and PS I results in water oxidation (producing oxygen) and NADP reduction, with the energy for this process provided by light (2 quanta for each electron transported through the whole chain).

Electron flow from water to NADP requires light and is coupled to generation of a proton gradient across the thylakoid membrane. This proton gradient is used for synthesis of ATP (adenosine triphosphate), a high-energy molecule. ATP and reduced NADP that resulted from the light reactions are used for $CO_2$ fixation in a process that is independent of light. $CO_2$ fixation involves a number of reactions that is referred to as the Calvin-Benson cycle. The initial $CO_2$ fixation reaction involves the enzyme ribulose-1,5-bisphosphate carboxylase/oxygenase (RuBisCO), which can react with either oxygen (leading to a process named photorespiration and not resulting in carbon fixation) or with $CO_2$. The probability with which RuBisCO reacts with oxygen vs. with $CO_2$ depends on the relative concentrations of the two compounds at the site of the reaction. In all organisms $CO_2$ is by far the preferred substrate, but as the $CO_2$ concentration is very much lower than the oxygen concentration, photorespiration does occur at significant levels. To boost the local $CO_2$ concentration and to minimize the oxygen tension, some plants (referred to as $C_4$ plants) have set aside some cells within a leaf (named bundle-sheath cells) to be involved primarily in $CO_2$ fixation, and others (named mesophyll cells) to specialize in the light reactions: ATP, $CO_2$ and reduced NADP in mesophyll cells is used for synthesis of 4-carbon organic acids (such as malate), which are transported to bundle sheath cells. Here the organic acids are converted releasing $CO_2$ and reduced NADP, which are used for carbon fixation. The resulting 3-carbon acid is returned to the mesophyll cells. The bundle sheath cells generally do not have PS II activity, in order to minimize the local oxygen concentration. However, they retain PS I, presumably to aid in ATP synthesis.

Thylakoid organization is very sophisticated in order to extract the energy from light, and to transfer this energy to a proper location, and/or dissipate the same. The transfer is rendered possible and efficient by separating electrical charges and a high capacity to regenerate a neutral electrical state, ready for undertaking again a change in charges (Blankenship et al. 1998).

The electron transfer between the above five main components is extremely rapid: the transfer from an activated P680 to pheophytin takes less than one picosecond. The electron transfer stops when all the pigments return to a neutral electrical charge, ready to undertake a new cycle.

Electrons are finally directed to a coupling factor to reduce NADPH, necessary in ATP synthesis, which will serve in sugar synthesis.

The term "thylakoids" is used hereinbelow and means to cover organized photosynthetic membrane components obtained from photosynthetic organisms, eucaryotic and prokarytotic. When the organism has chloroplasts, the thylakoids comprise the following membrane constituents: PSII, cytochromes $b_6$ and f, PSI and the coupling factor. Where thylakoids integrity and functionality has been tested from plant material, it has been measured between two reference points: proximal to PSII and distal to the coupling factor. For certain applications, thylakoids do not need to be active although they are apparently integral. Such thylakoids are performing and at least as stable as any other antioxidant. Therefore, "active thylakoids" means thylakoids having the capacity to activate upon hydration, as opposed to inactive thylakoids which are integral but which have been actively or passively inactivated. In this case, the reaction center is inactive although thylakoids structure is substantially preserved. The "inactive" thylakoids are therefore suitable antioxidants although they do not have the same dynamism nor do they have the same capability to regenerate, or the same capacity to respond to ROS as the active/activable form.

Photosynthesis comprises two fundamental processes that can be summarized in the two following reactions:

(1)

(2)

During the first reaction in the presence of light, protons are taken from chloroplast water to produce ATP. The second reaction consists in using NADPH and ATP in a series of reactions that lead to the reduction of carbon anhydride in glucides, mainly starch. These two reactions occur simultaneously; products formed by process (1) are directed into the reaction of process (2). Globally, the photosynthesis results into the production of sugars in the form of starch and sucrose and energy under the form of ATP molecules:

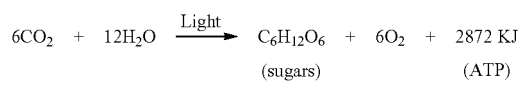

Light activation follows a certain pathway in the thylakoids. Light is first collected by light antenna (LHCII), and the energy is directed to reaction center (PSII) and, finally to PSI which also has an independent light collector (LHCI). Thylakoids have for functions to collect light and to transfer light energy to a proper location for further photosynthesis. The synthesis of ATP and of sugars does not take place in the thylakoids but in other chloroplast compartments.

Chlorophylls are the main active pigments. The carotenoids have more than one role, depending on their location. A first role is as light collectors, which results in energy transfer from carotenoids to chlorophylls. A second role is as photoprotectors, this time the energy transfer occurring in an opposite direction between chlorophylls and carotenoids. Carotenoid singlet state has more energy that a singlet chlorophyll while, on the opposite, carotenoid triplet state has less energy than triplet chlorophylls. The energy states having a natural tendency to go from a high to a low energy level, one will appreciate that the singlet carotenoid mostly acts as a light collector passing light energy to a singlet chlorophyll molecule while the triplet chlorophyll will readily transfer its energy to the triplet carotenoid, when the latter acts as a photoprotector in the reaction center. Carotenoids take different configurations upon associating with antenna or reaction center, which configuration may be responsible for their energy state upon activation. A "cis" configuration is associated with photoprotection in the reaction center. An "all-trans" configuration is associated with the light collector function of the antenna.

The transfer of energy is efficient only in conditions in which the pigments are very close to each other and in a specific organisation. It is therefore very important not to disturb the natural organisation of the pigments, keeping the membranes in an integral state, if one wants to purify active or fully activable thylakoids.

One advantage of recovering intact thylakoids is found in their capacity to handle ROS. Such ROS are intended to cover free radicals (including super oxides), as well as non-radical oxidants such as singlet oxygen ($^1O_2$) and peroxides. A good review of the definition and origin of these species is found in the international publication WO 94/13300. The contents of all the references cited hereinabove and below are incorporated herein by reference.

Free radicals are atoms, ions, or molecules that contain an unpaired electron. Free radicals are usually unstable and exhibit short half-lives. Elemental oxygen is highly electronegative and readily accepts single electron transfers from cytochromes and other reduced cellular components; a portion of the $O_2$ consumed by cells engaged in aerobic respiration is univalently reduced to superoxide radical ($.O_2^-$). Sequential univalent reduction of $.O_2^-$ produces hydrogen peroxide ($H_2O_2$), hydroxyl radical ($.OH$), and water.

Free radicals can originate from many sources, including aerobic respiration, cytochrome P-450-catalyzed monooxygenation reactions of drugs and xenobiotics (e.g., trichloromethyl radicals, $CCl_3$. formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H. and .OH. The hydroxyl radical, .OH, is the most reactive radical known in chemistry. It reacts with biomolecules and sets off chain reactions and can interact with the purine or pyrimidine bases of nucleic acids. Indeed, radiation-induced carcinogenesis may be initiated by free radical damage. Also for example, the "oxidative burst" of activated neutrophils produces abundant superoxide radical, which is believed to be an essential factor in producing the cytotoxic effect of activated neutrophils. Reperfusion of ischemic tissues also produces large concentrations of oxyradicals, typically superoxide. Moreover, superoxide may be produced physiologically by endothelial cells for reaction with nitric oxide, a physiological regulator, forming peroxynitrite, $ONOO^-$ which may decay and give rise to hydroxyl radical, .OH. Additional sources of oxyradicals are "leakage" of electrons from disrupted mitochondrial or endoplasmic reticular electron transport chains, prostaglandin synthesis, oxidation of catecholamines, and platelet activation. Many free radical reactions are highly damaging to cellular components; they crosslink proteins, mutagenize DNA, and peroxidize lipids. Once formed, free radicals can interact to produce other free radicals and non-radical oxidants such as singlet oxygen ($^1O_2$) and peroxides.

Singlet oxygen is a particularly noxious compound involved in the initiation or in the perpetuation of many diseases or disorders. The singlet oxygen is also involved in the degradation of protein like chlorophylls. This is why a photoprotection conferred by the presence of carotenoids becomes important. Carotenoids protect the chlorophyll life and activity, they further protect the integrity of the membranes by preventing protein denaturation Carotenoids are capable of capting the energy of triplet chlorophyll molecules; they become triplet carotenoid molecules, which regenerate themselves while dissipating heat thereby avoiding the accumulation of a triplet chlorophyll, and minimizing the chances to degrade the chlorophyll.

However, in the presence of excess light, damage may occur, which may originate from the formation of chlorophyll in "triplet state". In a triplet state two electrons in the outer shell have identical rather than opposite spin orientation. This triplet chlorophyll readily reacts with oxygen, leading to the very reactive singlet oxygen, which can damage proteins. To counter this damaging reaction, carotenoids are usually present in close vicinity to chlorophylls. Many carotenoids efficiently "quench" triplet states of chlorophyll, thus avoiding formation of singlet oxygen. Chlorophyll in its free form is very toxic in the light in the presence of oxygen, because a close interaction with carotenoids is not always available under such circumstances. Therefore, all chlorophyll in a cell in aerobic organisms is bound to proteins, generally with carotenoids bound to the same protein.

A major difficulty in measuring enzyme kinetics at relatively short time scales (less than 1 ms) is that "traditional" enzyme reactions require a mixing of substrate and enzyme, which usually takes a relatively long time. Kinetic analysis of light-driven reactions such as photosynthetic electron transport have a great advantage in this respect: reactions can be triggered simply by a light pulse, which can be even shorter than 1 ps. Moreover, many of the components participating in electron transfer have different absorption spectra depending on whether they are in the oxidized or reduced form. Using laser spectroscopy methods or more standard optical spectroscopy, it is relatively simple to follow the electron around on a timescale between 1 ps and several ms. The primary charge separation occurs in several ps, and reactions become gradually slower as they involve components that are further away from the reaction center. Because of the fast speed of early reactions, the electron and the "electron hole" are physically separated rapidly by a large distance (the electron generally has traveled about 2 nm to the other side of the membrane within 1 ns after charge separation), so that back reactions (charge recombinations) are not favorable anymore. Unpaired electrons on reactants that are transiently formed during redox reactions involving transfer of a single electron in many instances can be detected using electron paramagnetic resonance (EPR) and derived techniques (including ENDOR, electron nuclear double resonance, and ESEEM, electron spin echo envelope modulation). Many of these techniques can be used to kinetically follow redox reactions, and provide detailed information regarding electron spin distributions etc. Therefore, photosynthetic membranes and reaction centers have a prominent place as experimental systems in biochemistry and biophysics.

The anti-oxidative potential of a compound such as chlorophyll is examplified in equation (1)

$$^3Chl^* + ^3O_2 \rightarrow Chl + ^1O_2^*  \quad (1)$$

Chlorophyll that has been excited into presence of oxygen becomes in a triplet state ($^3Chl^*$), and disactivates to return to a fundamental state by producing singlet oxygen (a noxious species) in cells. Plants have found an efficient means by which they can solve the problem of overproduction of singlet oxygen. The plants transfer the chlorophyll energy to another pigment which has an inferior energy state. That pigment called carotenoid (equation 2) is abundant in plants.

$$^3Chl^* + Car \rightarrow Chl + ^3Car^*  \quad (2)$$

Although triplet chlorophyll has more energy than a corresponding carotenoid, the converse is true for the singlet state. As shown in equations 3a and 3b, an activated singlet carotenoid transfers its energy to a chlorophyll molecule which becomes activated in a singlet state.

$$Car + energy \rightarrow ^1Car^*  \quad (3a)$$

$$^1Car^* + Chl \rightarrow Car + ^1Chl^*  \quad (3b)$$

Carotenoids in a triplet state desactivates without forming a noxious oxygen species. Equation 4 shows that carotenoids inactivate by returning to a fundamental state and by heat dissipation.

$$^3Car^* \rightarrow Car + Heat  \quad (4)$$

It appears that it is important not to produce ROS to preserve the properties of the pigments in an extract, but it is also important to remove those ROS that may be generated during isolation. For achieving this, we have given favor to a way to reverse the equilibrium of equation 1. Consequently, the converse equation 1 is found in equation 5.

$$Chl + ^1O_2^* \rightarrow ^3Chl^* + ^3O_2  \quad (5)$$

To avoid reversal of equation 5, activated triplet chlorophyll molecule needs to be in close contact with a carotenoid in its fundamental state, which takes the transferred energy and dissipates the latter as heat. This way the reversibility of equation 5 is restricted insofar as chlorophyll and carotenoid pigments can be found in very close proximity so as to transfer to one another their energy.

From the above equation 5, it is apparent that, to obtain an extract that is optimally active, it is preferable to take every possible measures to maintain both pigments (chlorophyll and carotenoid) in their fundamental state. Isolated carotenoids, e.g. carotenoids not organized in thylakoid structures, would not be capable of an efficient quenching of triplet chlorophyll molecules. The advantage of having organized pigments is that the extract will retain the dynamism of natural thylakoid membranes, which confers to them the capacity to capture ROS, to transfer the energy and to return to a state capable of undertaking new activation cycles again. This dynamism and capacity to regenerate is unique to organized pigments. It is important to mention that the above reactions are spontaneously produced and this, in absence of light. This observation is important from a therapeutic point of view, because internal administration of a thylakoid extract would preclude the presence of light.

Thylakoids having optimized configuration and carotenoid proportions will retain full activity especially toward ROS. Such an antoxidant will be useful to reduce the expression of diseases or disorders that involve the production of ROS. Such diseases or disorders can be those with an etiology related to inflammation, cancer and contact with radiations. Such diseases or disorders comprise those affecting Skin: such as burns, solar radiation, psoriasis, dermatitis; Brain: such as trauma, stroke, Parkinson, neurotoxins, dementia, Alzheimer; Joints: such as rheumatoid arthritis and arthrosis; Gastrointestinal tract: such as diabetes, pancreatitis, endotoxin liver injury, ischemic bowel; Eye: such as cataractogenesis, retinopathy, degenerative retinal damage; Vessels: such as atherosclerosis and vasculitis; Erythrocytes: such as Fanconi anemia, malaria; Heart: such as coronary thrombosis; Lung: such as asthma, COPD; Kidney: such as transplantation, glomerulonephritis; Multiorgan: such as inflammation, cancer, ischemia-reflow states, drug toxicity, iron overload, nutritional deficiencies, alcohol toxicity, radiation, ageing, amyloid diseases and toxic shock. The literature related to the involvement of ROS in some diseases is the following:

| Skin: | Burn | Youn, 1992 |
|---|---|---|
|  | Solar Radiation | Golan, 1994 |
|  | Psoriasis | Lange, 1998 a, b |
|  | Dermatitis | Polla, 1992 |
| Brain: | Trauma | Juurlink, 1998 |
|  | Stroke | El Kossi, 2000 |
|  | Parkinson | Ebadi, 1996 |
|  | Neurotoxins | Foler, 2000 |
|  | Alzheimer | Smith 2000 |

-continued

| | | |
|---|---|---|
| Joints: | Rheumatoid arthritis | Cimen, 2000 |
| Gastrointestinal tract: | Diabetes | Gerber, 2000 |
| | Pancreatitis | Sakorafas, 2000 |
| | Endotoxin liver injury | McGuire, 1996 |
| | Ischemic bowel | Lai, 2000 |
| Eye: | Cataractogenesis | Eaton, 1994 |
| | Retinopathy of prematurity | Hardy, 2000 |
| | Degenerative retinal damage | Castagne, 2000 |
| Vessels: | Atherosclerosis | Singh, 1997 |
| Erythrocytes: | Anemia | Anastassopoulou, 2000 |
| | Malaria | Ginsburg, 1999 |
| Heart: | Coronary thrombosis | Chen, 1995 |
| Lung: | Asthma | Montuschi, 1999 |
| | COPD | Montuschi, 2000 |
| Kidney: | Glomerulonephritis: | Barros, 2001 |
| Multiorgan: | Transplantation | Jonas, 2000 |
| | Inflammation | El-Kadi, 2000 |
| | Cancer | Prior, 2000 |
| | Ischemia | Lewen, 2000 |
| | Drug toxicity | Sinha, 1990 |
| | Iron overload | Karbownik, 2000 |
| | Nutritional deficiencies | Olszewski, 1993 |
| | Alcohol toxicity | Lieber, 1997 |
| | Ageing | Cadenas, 2000 |
| | Radiation | Bednarska, 2000 |
| | Amyloid diseases | Floyd, 1999. |

Besides therapeutic applications, it has been found that the thylakoids of this invention may advantageously replace chloroplasts-derived compositions of the art that have been tested as biosensors or biofilters or bioreactors. The art in the field teaches these specific uses, but the chloroplasts-derived compositions lack stability and degrade very rapidly, which renders these uses unpractical from a commercial point of view. Therefore, a stable and dynamic thylakoid extract could advantageously substitute for these non-performing chloroplasts-derived compositions.

Biosensors:

Detection of toxic products is valuable for evaluating environmental risks associated with the presence of contaminants. Valid bioassays would normally involve living organisms and would fulfill the following minimal conditions:
i) they should be representative of the natural environment,
ii) they should reproducible,
iii) they should be reliable so as to provide no or almost no false results; and
iv) they should be sensitive.

Toxicity detection should also provide enough flexibility for analyzing different types of contaminated samples. Toxicity should be ideally monitored and sensed in real time fashion. Toxicity detection finds application in at least three industrial sectors: paper industry, contaminated soil analysis and agriculture. In all these instances, information is needed on the presence of contaminant in order to rapidly correct an undesirable situation.

A major problem encountered with the actual technologies to sense toxic products is in the long delay of obtention of the results of biotests from 48 to 96 hours, when using organisms like trout or *Daphnea magna*. A good detecting device would be one distinguishing from the available conventional biotests by the use of material which would allow measurements of a contaminating potential of an effluent in real time and continuously. Although some biodetectors are commercially sold, which measure fluorescence generated by plant photosynthetic activity, a system that would permit measurement of electrical charges induced by the presence of light, and modulated by the presence of contaminants would be ideal. This technology would be much cheaper than the fluorimetric technology. It is believed that a technique which would evaluate the photosynthetic activity on a total thylakoid material would be preferable over fluorometric methods which measure the activity of a specific proteic complex, namely the PSII. A device comprising thylakoid material would therefore have the advantage of measuring the toxicity in a larger spectrum of action. Such as detecting device would measure the number of electrons produced with a given light intensity. A current ($Ep_{max}$) obtained after a few seconds should be proportional to the photosynthetic activity of the thylakoids. If the photocurrent is plotted against the concentration of contaminants, a typical sigmoidal should be obtained, upon which an estimated $EC_{50}$ should be deduced.

A photocurrent has been already measured by Allen and Crane in 1976. It has been found that electron transport constituted a reliable and representative measure of global photosynthetic activity and of the physiological health of a plant From the work of Allen and Crane, it is conceivable that an extract that would have a great stability, along with a dynamism and capacity to regenerate its responsive state to contaminants and light would be highly preferable over the known devices. A detector would measure the number of electrons produced at a given light intensity. A maximal photo-current value ($Ip_{max}$) obtained after a few seconds is proportional to the photosynthetic activity of the thylakoid membranes. If one plots $Ip_{max}$ v. the concentration of a photosynthetic inhibitor (a contaminant or a pollutant) present in the photoconversion chamber, a typical sigmoidal curve is obtained. The inhibitor potency can be easily evaluated ($IC_{50}$).

A detecting device would comprise: a white light source, a photoconversion chamber receiving two electrodes, a detecting means for measuring electrical currents induced by light and computer means for collecting and processing data (electric currents). A liquid sample comprising a toxic agent, a contaminant or a pollutant to be identified or measured, is contacted with a thylakoid membrane extract. Once the mixture introduced in the chamber, a brief illumination is applied (less than one minute). The device or apparatus may be conceived to process and analyze a plurality of samples simultaneously.

Biofilters/Bioreactors:

Because the photosynthetic apparatus in plants is capable of not only capturing photons, but also of capturing and accumulating molecules having affinity for its components, it is contemplated that the present extract would also have the same capacity as the plant itself. Moreover, since some of the captured molecules may be processed, the present extract would act as a bioreactor. The molecules susceptible to be captured are, for example, herbicides, insecticides, fungicides, urea, ions and heavy metals as well as gas like $O_3$, $CO$, $H_2S$, $NO$, $CO_2$, $O_2$ .... The biofilter of this invention would be versatible and would be resistant to temperature variations.

There is no existing practical process in the art teaching how to recover intact functional thylakoids, capable of retaining activity for a practical amount of time.

It is obvious from the above that the plants have a great natural capacity to manage with threatening situations. The thylakoids are particularly adapted to resist and adapt to such extreme situations.

The U.S. Pat. No. 4,698,360 describes a plant extract comprising pro-anthocyanidins useful as free-radical scavengers. The process of making this extract comprises the following steps:
a) the obtention of a coarse powder of maritime pine bark;
b) its extraction in boiling water;
c) a separation of liquids from solids;
d) cooling the liquids to ambient temperature;

e) a filtration;
f) a "salting-out" precipitation to remove undesirable matter;
g) extracting active ingredients into ethyl acetate;
h) drying the organic phase;
i) resuspending the solids and reprecipitating the active ingredients with chloroform; and
j) resuspending the solids before advanced purification.

This reference is concerned with the isolation of a specific type of active ingredient, and not with the preparation of thylakoids that would contain a major portion of its photosynthetic components, in other words wherein pigments would not be separated from each another.

This reference is indeed typical of the overall teachings in the general art which the present invention pertains to. The prior art relates systematically to the isolation of one or more given plant components, and not to the isolation of intact thylakoids comprising a major portion of their constituents preserved in an integral and functional state.

Glick et al. (1985) in Planta 164: 487-494 describe the variations in stoichiometric ratios of photosystems II and I (PSII/PSI) when peas are submitted to different types of light. The electron transport capacity of PSI and PSII in the presence of indicators such as 2,5-dimethyl-p-benzoquinone and NADP, which are indicators specific for PSII and PSI, respectively. Although green light is used, which is a non-activating light environment, it is not used to condition the plant in a process which aims at isolating intact and activable thylakoids. The reference essentially relates to the study of the composition of chloroplasts and not the preservation of thylakoids activity in function of a given light quality and intensity. The plants are rather conditioned in different lights that are depleted or enriched in red wavelengths. This reference is not concerned with the fact that the photosynthetic pigments should be kept close to each other so as to favorise the energy transfer between chlorophylls and carotenoids and to favorise free-radicals capture. Thus the conditions leading to the isolation of photosynthetic pigments in their natural state in thylakoids are not specifically taught and met with in this reference.

Mason et al. (1991) in Plant Physiol. 97: 1576-1580 teach a method for isolating chloroplasts, which makes use of a step of forced passage of a plant suspension through a 27-needle at a flow speed of 0.5 ml per second, rather than using a dispersion step by homogenization. The plant solution comprises a buffer having a pH 7.5 and comprising 0.3 M sorbitol. The preparation that has been forced through the needle is centrifuged in a Percoll gradient and the chloroplasts are separated from other constituents, including thylakoids. This process is therefore different from the present process which aims essentially at the recovery of thylakoids using quite simple steps and reactants, which present process being also easy to scale up. The light conditions are not mentioned in this reference. Further, the conditions to keep chloroplasts integral are obviously not the same as conditions to disintegrate chloroplasts. In the present process, the chloroplasts are disintegrated but thylakoids membranes are recovered substantially intact. This reference therefore cannot teach the present invention.

The Canadian patent application 2,110,038 describes a process of stabilizing plant extracts. These extracts are however cell fluids or juices and not thylakoid membranes. There is no mention in this reference of withdrawal of water as a natural electron donor from the membranes, for the purpose of stabilizing thylakoids.

In view of the foregoing, no practical process has been taught in the art, that would lead to the isolation of intact and functional thylakoid membranes. There is further no teaching of conditions for stabilizing thylakoid components. There is finally no teaching of the use of isolated thylakoid membranes to scavenge cell components from ROS.

There is therefore an open challenge in developing a process for obtaining active thylakoids that remain integral and, optionally activable, for an acceptable amount of time and which, upon reactivation are capable of acting as an antioxidant by their ROS scavenging activity. Although an increasing body of literature is available on photosystem components, nobody has published a practical process wherein the conditions of isolation and preservation of thylakoid activity are taught.

Moreover, since free radicals may be responsible for the degradation of many cell components, it is expected that their capture would protect other plant constituents. The present process would therefore produce an improved yield of plant components other than thylakoids.

Because there is a demand for powerful antioxidants, particularly in the pharmaceutical field, a process providing any such antioxidants, as well as the antioxidants per se capable of a good potency as well as of a sustained activity, would be greatly appreciated. Further, there is a demand for biological material useful as sensors or detectors, captors or filters, bioreactors or biological molecule producers.

SUMMARY OF THE INVENTION

The present invention aims at providing a simple process for obtaining an extract having functional thylakoids. The present invention also provides a process wherein the thylakoids are purified from other cell components. It is another object of this invention to provide a stabilized extract comprising non-isolated or isolated thylakoids. The stabilized extract is essentially free of any electron donor which would activate the thylakoids. Since the most abundant electron donor is water, the stabilized extract is therefore preferably water-free. Water can be chased by a solvent or by drying, for example. An amphoteric solvent, particularly a surfactant such as propylene glycol has been tried with success. This type of solvent does not disintegrate the membrane structural components, and has the advantage of replacing water molecules and of preventing the formation of aggregates upon redissolution in an aqueous solution. The stabilized extract has a longer shelf life with no substantial loss of activity as long as no electron donor such as water is added thereto. The stabilized extract is rehydrated extemporaneously before use to start the activation. The activity of extract once activated, lasts much longer than any other known antioxidant, which indicates a certain level of regeneration of activity rather than immediate and complete exhaustion. Further the antioxidant potency adapts, thus increases or decreases, upon the extent of the oxidative insult.

In accordance with the present invention, is provided a method as defined in claim 1.

This invention provides a method of obtaining an extract obtainable from photosynthetic organisms comprising thylakoids, the method comprising the steps of:
a) providing a suspension of organism constituents that contains thylakoids; and
b) disrupting the constituents while maintaining thylakoids intact in a medium having a viscosity comprised between 1 to 1.3 centipoise and pH above 2 and below 10; the medium being added in a volume calculated upon the following equation:

$$(\text{Volume of medium} + \text{plant constituents water content})/\text{Plant constituents dry weight} > 10$$

whereby a first extract essentially constituted of thylakoids, cells debris/membranes and a liquid phase is obtained, said thylakoids comprising integral photosynthetic pigments.

Preferably, the resultant of the above equation would be comprised between 25 and 150.

The pH of the medium is preferably comprised between 5 and 8, more preferably between 7 and 7.5.

The suspension of step a) may be obtained by mechanically dispersing organism constituents or tissues in said medium.

In a preferred embodiment, step a) is preceded by a step of submitting said organism to a conditioning parameter selected from light, osmotic stress, heat, cold, freezing, dryness, hormones, chemical and biological inducers.

In a most preferred embodiment, step a) is preceded by a step of conditioning said organism in a light environment of a wavelength comprised between about 500 and 600 nm, and step b) is performed under the same light environment.

The viscosity is partly achieved by adding a sugar. The sugar may be added in concentration as high as 1.5M and over. Preferably, a sucrose concentration of about 0.2 to 0.4 M in said solution or a sugar achieving a viscosity equivalent to 0.2 to 0.4 M sucrose.

A specific example of a medium used in the above method is: Tris or acetate or ascorbate buffer (20 mM, pH 7.0-7.5), and sorbitol or sucrose 350 mM.

The method of this invention may further comprise the following step c): separating thylakoids, cell debris/membranes and liquid phase from each another, to form a second, third and fourth extracts essentially constituted by isolated thylakoids, cell debris and membranes, and liquid phase, respectively.

The step of separating has been particularly performed upon a difference of sedimentation coefficient of each of thylakoids, cell debris and membranes, and liquid phase.

A specific example of such separating step comprises centrifuging the first extract for 10 minutes at 10 000 g in a tube equipped with a filter in a superior portion of the tube, the filter having a suitable porosity onto which cell debris and membranes deposit while the thylakoids and the liquid phase pass through the filter, the thylakoids forming a pellet in an inferior portion of the tube. Alternatively, gross purification may be achieved by recovering cell debris and membranes first by pressing and/or filtering, for example, followed by a finer purification, e.g. separating thylakoids from the liquid phase.

After separation, each first to four extracts may be stabilized by adding the following step d): eliminating any electron donor from said extracts so as to inactivate and stabilize the photosynthetic pigments preferably in the presence of sugars (which may protect components against cold). The second and third extracts are particularly targeted by this step.

The first contemplated electron donor is water, so the extracts are processed to be water free.

Water may be eliminated under vacuum freeze drying or by exchanging it against a non-denaturing amphoteric solvent or surfactant after step c), non-denaturing meaning not capable of dissociating or of damaging the thylakoid structural components.

An amphoteric solvent which has been tried with success is propylene glycol.

It is further another object of this invention to provide products that result from the above process. A pure thylakoid extract having the capacity to be activable is first provided. A stabilized extract is preferred. The above third extract being rich in thylakoids and cellulosic material is also within the scope of this invention, namely in a stabilized form. The stabilized form for thylakoids may be dried or in a medium composed of an amphoteric solvent such as propylene glycol. The former is in an insoluble state or suspension; the latter forms a solution. Thylakoids comprising extracts are reactivated in the presence of an electron donor. The first contemplated electron donor is water. Once activated, the extracts act as dynamic scavengers of ROS.

For nutraceutical, cosmeceutical and pharmaceutical applications, this scavenging activity results in the treatment or the prevention of diseases or disorders that are mediated by the formation of ROS, especially those having an etiology related to inflammation, cancer, or contact with radiations.

A first scavenging and protecting effect is exploited against radiations that are in the ultraviolet spectrum. Therefore topical use for the thylakoids and topical compositions comprising the thylakoids are within the scope of this invention.

It has been found that thylakoids have the capacity to form a photon-absorbing film or coating on a body surface like skin or mucosa. This property appears to be independent from the ROS scavenging activity. The extracts comprising thylakoids, in an activable form or not, therefore act as a filter for radiations, namely in the ultraviolet range. When the extracts further have functional thylakoids, they have a dual role as U.V. filter and as a ROS scavenging compound. The extracts may be used further in a method or a composition or a device for detecting, for capturing molecules or for producing or processing molecules having affinity for thylakoids or interfering with their activity.

Examples of such molecules are herbicides such as triazines (ex. atrazine- and diuron-type herbicides), quinones, chlorpromazine, urea, formaldehyde, alkylamino cyanoacrylates, trypsin, cyanoacrylate, Tris, adenine derivatives, disulfiran (metal chelator), acetyl CoA carboxylase, digitonin, heavy metals (ex., Cu, Zn, Cd, Pb, Hg . . . ), $SO_2$, $NO_2$, $NH_2OH$, $CO_2$, $CO$, $O_3$, $O_2$, $H_2S$, calcium antagonists (calmodulin-type), sulfate, sulfite, bisulfite, nitrite, acetate, lactate, anions such as $NO_3^-$, $HCO_3^-$, $HCO2^-$, $F_-$, $NO_2^-$, $HS0_3^-$, . . . .

DESCRIPTION OF THE INVENTION

This invention will be described hereinbelow, referring to specific embodiments and the appended figures, the purpose thereof being to illustrate this invention rather than to limit its scope.

DESCRIPTION OF THE INVENTION

This invention will be described hereinbelow, referring to specific embodiments and the appended figures, the purpose thereof being to illustrate this invention rather than to limit its scope.

BRIEF DESCRIPTION OF THE DRAWINGS

FIG. 8 shows the relative activity of the extract of the present invention in function of the proportion of propylene glycol (propane 1,2 diol) included in the resuspension solution.

FIG. 11 illustrates the protection exerted by the extract of the present invention (dilution 1:1000) on IMR-32 cells against damages caused by two concentrations of TBHP; FIG. 11b): 50 µM.

FIG. 12 represents the protection exerted by two different dilutions of the extract of the present invention on IMR-32 cells after TBHP treatment.

Figure 1:
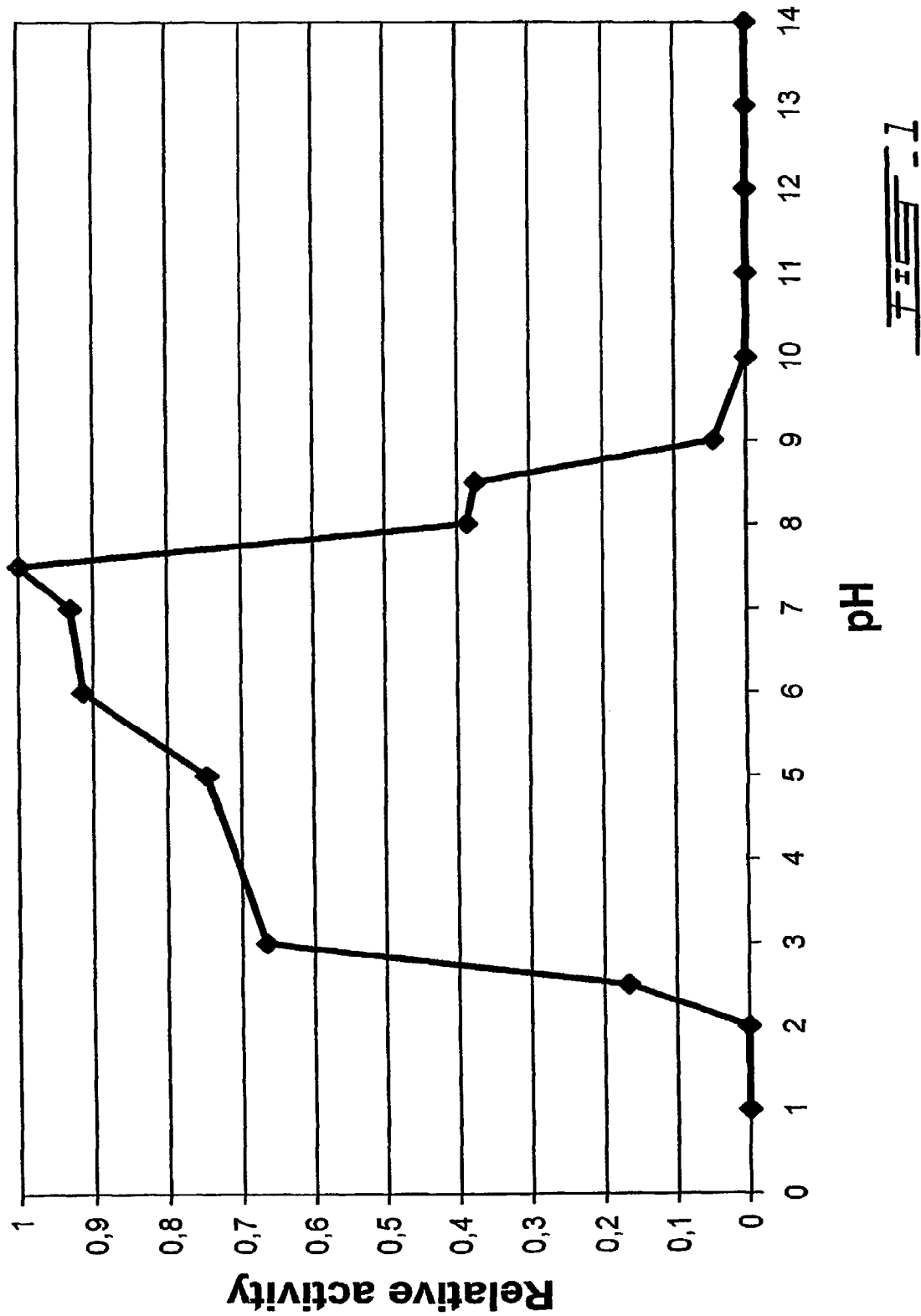
FIG. 1 represents the relative antioxidant activity of the extract of the present invention in function of the pH of the exogenous extraction fluid.

As used herein, an "antioxidant" is a substance that, when present in a mixture or structure containing an oxidizable biological substrate, significantly delays or prevents oxidation of the biological substrate. Antioxidants can act by scavenging biologically important reactive free radicals or other ROS (singlet oxygen, .O2-, $H_2O_2$, .OH, HOCl ferryl, peroxyl, peroxynitrite, alkoxyl . . . ), or by preventing their formation, or by catalytically converting the free radical or other ROS to a less reactive species.

The antioxidant of the present invention is considered as such if, when added to a cell culture or assay reaction, it produces a detectable decrease in the amount of a free radical, such as superoxide, or a nonradical ROS, such as hydrogen peroxide or singlet oxygen, as compared to a parallel cell culture or assay reaction that is not treated with the antioxidant. Suitable concentrations (i.e., efficacious doses) can be determined by various methods, including generating an empirical dose-response curve, predicting potency and efficacy of a congener by using QSAR methods or molecular modeling, and other methods used in the pharmaceutical sciences.

The present invention is intended to be used in the medical field to treat, prevent, or alleviate the symptoms associated with a ROS, associated disease or disorder or reduce the expression of such disease or disorder. Such a disease or disorder refers to a condition of an individual that results at least in part from the production of or exposure to free radicals, particularly oxyradicals, and other "ROS" in vivo. Even though there is only a few if any pathological conditions that are monofactorial, there is an increasing body of literature and knowledge related to the involvement of ROS in disease etiology. For these reasons, the term "ROS associated disease" encompasses pathological states that are recognized in the art as being conditions wherein damage from ROS is believed to contribute to the pathology of the disease state, or wherein administration of a free radical inhibitor (e.g., desferrioxamine), scavenger (e.g., tocopherol, glutathione), or catalyst (e.g., SOD. catalase) is shown to produce a detectable benefit by decreasing symptoms. increasing survival, or providing other detectable clinical benefits in treating or preventing the pathological state. For example but not limitation, the disease states discussed herein are considered ROS-associated diseases (e.g., ischemic reperfusion injury, inflammatory diseases, systemic lupus erythematosis, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness. Further, many inflammatory diseases or disorders will benefit of the present invention, since it is known that ROS intervene in the process of inflammation. For example, the "oxidative burst" of activated neutrophils produces abundant superoxide radical, which is believed to be an essential factor in producting the cytotoxic effect of actived neutrophils. Further, since neutrophils are involved in the early mortality of any grafted or transplanted tissue or cell, an antioxidant would increase the early survival of transplanted or grafted cells, which is critical for the success of transplantation.

DESCRIPTION OF THE PREFERRED EMBODIMENTS

The present invention relates to isolated thylakoids and a method for isolation of thylakoids, that will constitute a powerful antioxidant molecule having a scavenger activity towards ROS. This antioxidant is of a natural origin; it should have no toxicity or adverse effect, when employed in a reasonable concentration. This antioxidant can also be stabilized, which ensures stability over time, thus a reasonable shelf-life. Stabilization is performed by withdrawing electron donors (namely water molecules), which make thylakoids to stay in a quiescent form. Thylakoids are activated by adding an electron donor (namely through hydration).

Preparation or Conditioning:

A first step undertaken, before going through the steps for recovering the thylakoids in a crude suspension, may be a conditioning step. This conditioning is optional and permits to vary the compositions of the extracts. To optimize the levels of pigments in their non-activated state (namely chlorophyll and carotenoids), a conditioning step may be performed in the same conditions as the working conditions, e.g. under green light or in the dark. Under such circumstances, the chlorophylls are preferably in a singlet state while the carotenoids are preferably in a fundamental state. This way, when ready to use, the carotenoids will be activated and ready to take the energy coming from a triplet chlorophyll (photoprotection).

It is also possible to further protect the thylakoid pigments by adding other xanthophylls such as violaxanthin in the medium of extraction or to increase the number of carotenoids by working under a light having a narrow range of wavelengths (465-475 nm).

It is further also possible to enrich the organism, namely a plant, and its extracts, in some particular constituents by submitting the organism to a conditioning step other than light conditioning. Such other conditioning comprises osmotic stress, heat, cold, freezing, dryness, hormones, and chemical and biological inducers. All these conditioning parameters lead to a response in sensitive organisms, which then become enriched in said some particular constituents.

As an example of this, a heat treatment would promote the accumulation of heat shock proteins, that are useful for treating ROS-related diseases or disorders (namely arthritis). The main objective of the steps of the present process is to preserve the integrity of some valuable constituents, namely the molecular constituents of thylakoids, and to control the state of the molecules, preferably in their fundamental functional state.

Obtention of a Crude Extract:

When one starts with whole organisms or tissues thereof, such as plant tissues or whole plants, the first step of the process is a dispersing step such as a homogenization step. The plant tissues are, for example, pulverized mechanically. The mesophylium tissues (leaves or needles) may be cut into small pieces with the aid of a rotative knife such as that retrieved in a homogenizer or a commercial rotative cutter. Any means leading to the dissociation of the cellulosic material to uncover the thylakoids would be suitable.

Besides working under a light source which optimally minimize the light flux (green light, $\lambda$=500-600 nm), the working conditions would ideally comprise a working temperature of about 2 to 20° C., preferably less than 4° C., for the purpose of increasing the cell density and of preventing any degradation by enzymes. The working conditions also include hypertonic conditions using hypertonic agents such as sugars. These conditions achieve optimal viscosity and fluidity. A specific example of a homogenization buffer is as follows:

Homogenization Medium

| Volume, weight | Product | pH | Final Molarity |
|---|---|---|---|
| 6 ml | Tris Buffer (1M) | 7.0 | 20 mM |
| 50 ml | Sorbitol (2M) | | 330 mM |
| 1.5 ml | MgCl$_2$ (1M) | | 5 mM |
| 243.5 ml | H$_2$O | | |
| 300 ml | Total | | |

The pH of the solution can vary from above 2 to below 10 preferably from 5 to 8, more preferably maintained at a near neutral value of 7-7.5 (FIG. 1).

Figure 2:
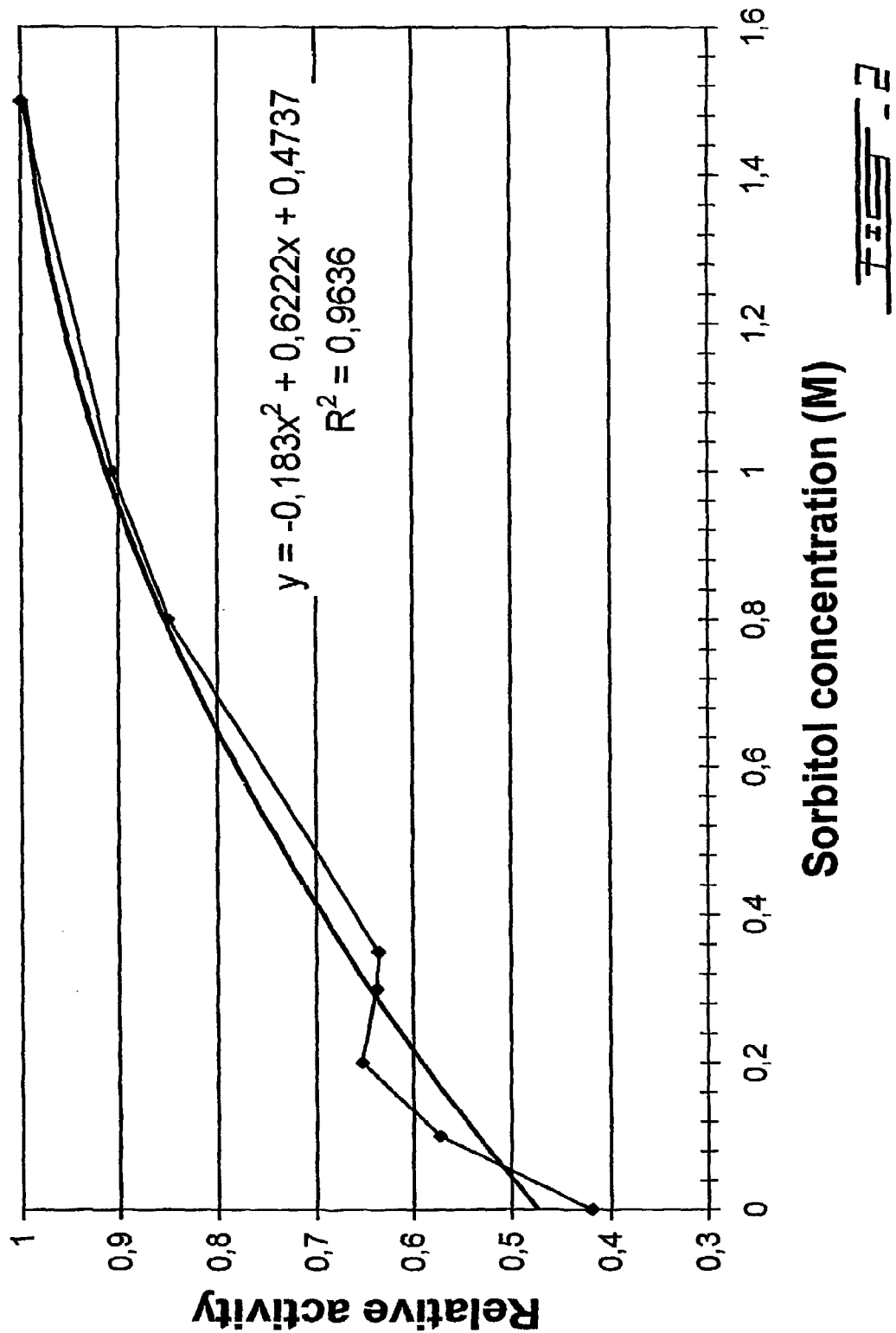
FIG. 2 shows the relative activity of the extract of the present invention in function of the sorbitol concentration included in the extraction fluid.
Figure 3:
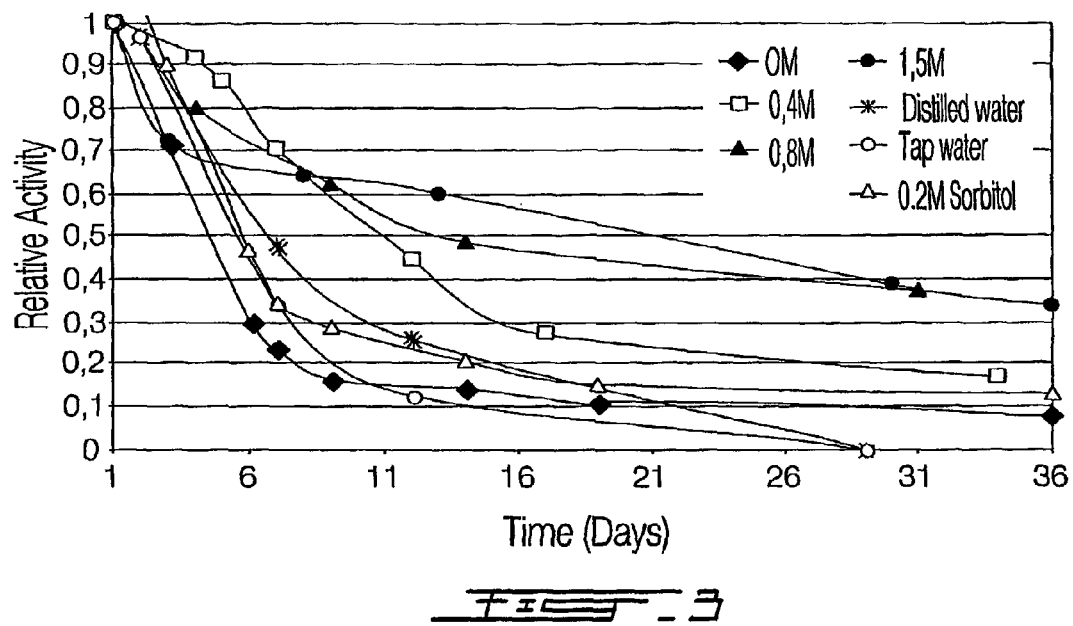
FIG. 3 shows the relative activity of the extract of the present invention in function of time and of the sugar concentration in the extraction fluid. Each sample was kept at −20° C.
Figure 4:
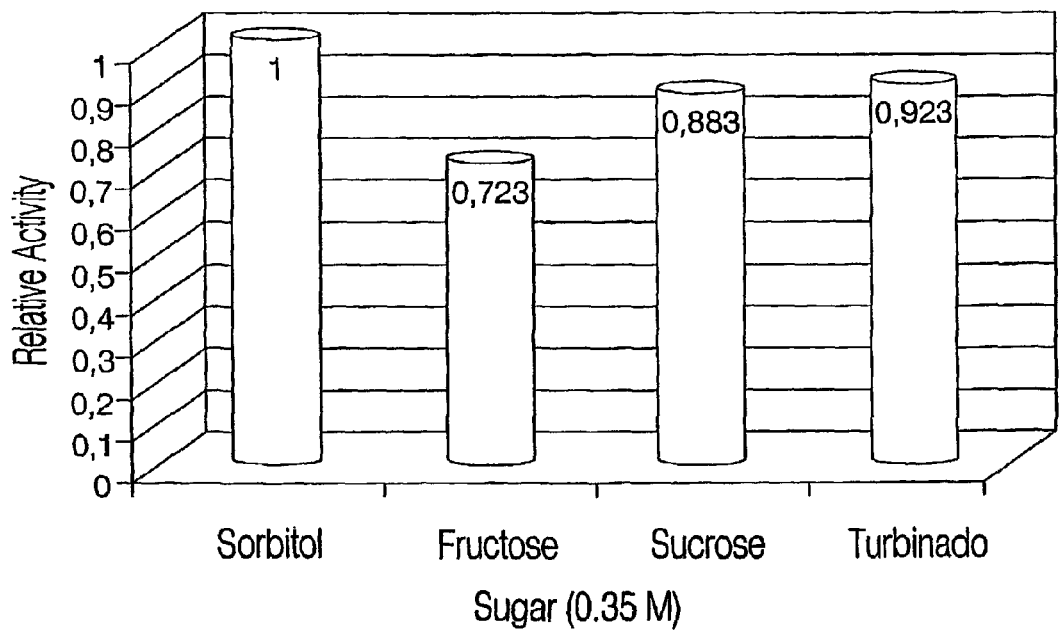
FIG. 4 represents the relative activity of the extract of the present invention in function of the nature of the sugar in the extraction fluid.
Figure 5:
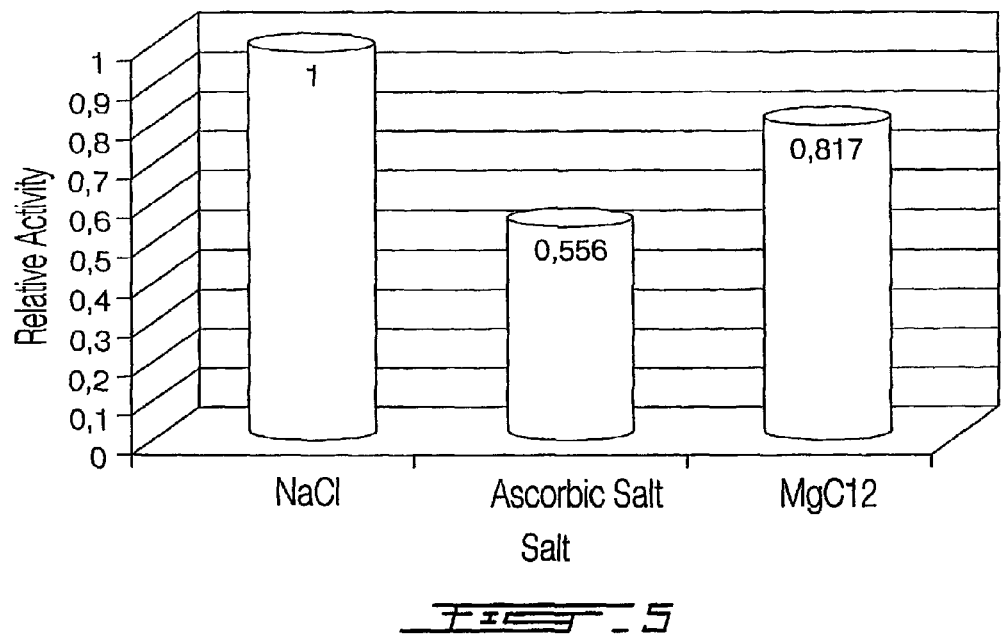
FIG. 5 shows the relative activity of the extract of the present invention in function of different salts used for extraction.

Taking spinach as a reference plant, the ratio wet weight of plant leaf tissues (g)/volume Of buffer (ml) is of about 1/3. Thus, the above recipe is suitable for extracting thylakoids from 100 g of spinach. The plant is mixed with the buffer and homogenized for example, in a domestic blender for about 30 seconds. The plant source may vary, so does the medium volume. The buffer itself may be any one suitable for maintaining a near neutral pH. For example, the above Tris buffer may be replaced with an acetate or ascorbate buffer. Both substitute buffers are acceptable for human consumption and ascorbic further has the advantage of providing vitamin C to the consumer. The sorbitol has been added to preserve the integrity of the membrane (FIGS. 2 and 3) and to insure a viscosity varying from about 1 to 1.3 and may be replaced by any other suitable sugar such as commercial saccharose, fructose or turbinado in a concentration achieving the same effect as 0.2 to 1.5 M (preferably 0.2-0.4 M) sorbitol. Sucrose 0.2-0.4 M would be an acceptable less expensive component (FIG. 4). Buffer components such as MgCl$_2$, NaCl, ascorbic salt/acid are not believed to be necessary to the present process, but they may help recovery more activity or preserving the activity for a long period (FIG. 5).

Figure 6:
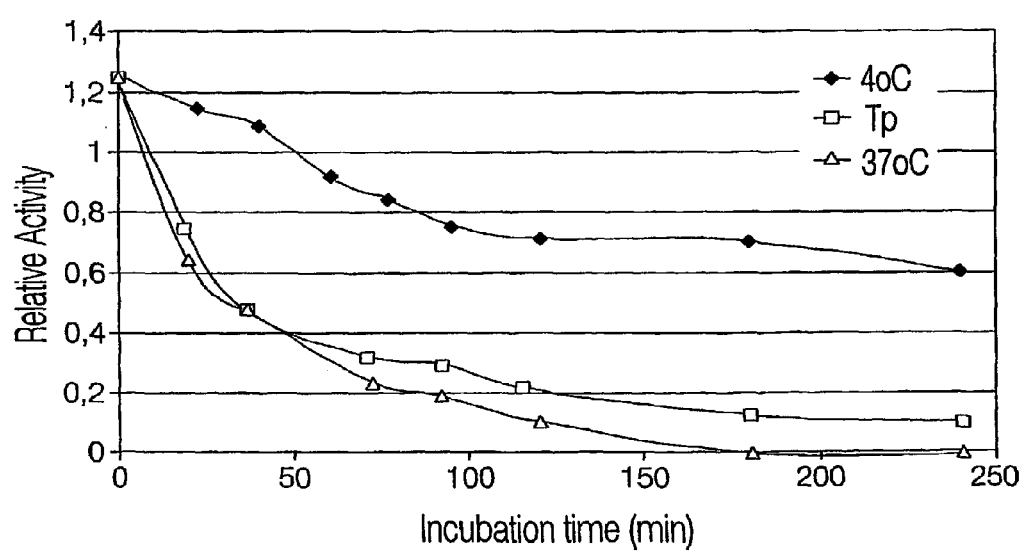
FIG. 6 represents the relative activity of the extract of the present invention (FRTS non-stabilized) in function of time and temperature.

A near neutral pH was preferably selected for maintaining an optimal concentration of H$^+$ ions. Sugars and pH are important parameters for preventing the dissociation of photosynthetic pigments. The density of cell fluids is maximized when working in a cool or cold environment, namely below 4° C. (see FIG. 6, wherein FRTS/1 stands for the present extract). Low temperatures also may protect components from enzymatic degradation. All these homogenization-conditions release the membrane structure from its organization in chloroplasts without substantially affecting the molecular structural organization of thylakoids. The chloroplasts are therefore disorganized without destroying or disintegrating the thylakoids. The surface of cell components without any cellulosic protection is thus increased.

It was convenient in the present process to use plant tissues directly in an extraction medium. However, if it becomes advantageous to use pure chloroplasts or a preparation enriched in chloroplasts or even preparation of other photosynthetic organisms having or not chloroplasts, it is feasible to do so. Cultured cells or tissues can also obviously replace whole plants.

Starting from spinach leaves, the yield of thylakoids is fairly good when one follows the following equation:

$\alpha/\beta>10$ $\alpha$=ratio of wet weight/dry weight; and $\beta$=ratio of wet weight/(Volume of medium+plant constituents water content).

So:

$$\frac{\text{(Volume of medium+ plant constituents water content)}}{\text{Plant constituents dry weight}} > 10$$

And more precisely (, preferably)

$$\frac{\text{(Volume of medium+ plant constituents water content)}}{\text{Plant constituents dry weight}} = 25\text{-}150$$

It is worthwhile noting that the yield may vary depending on the volume of buffer that was selected and on the water content of the selected plant. For example, pine needles have an endogenous water content that is much less important than in the case of spinach leaves. For an equal wet weight of plant material the volume of buffer should be increased for isolating thylakoids from pine needles, when compared to the spinach leaves, taking into account all the parameters of the above equation.

The crude extract obtained alone constitutes a first fraction that can be used per se, dehydrated, or further fractionnated.

Figure 7:
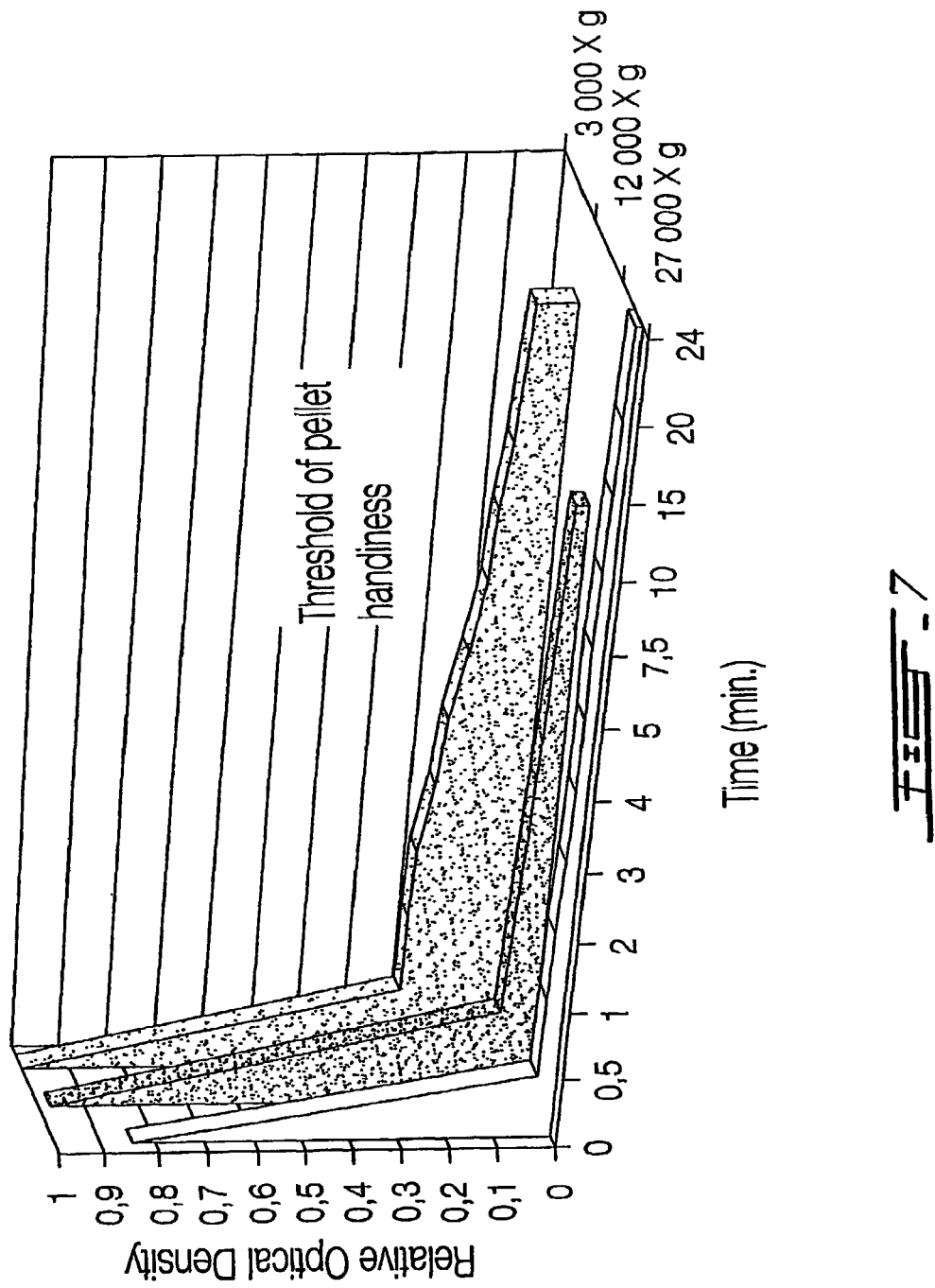
FIG. 7 shows the selection of centrifuge conditions for optimization.
Figure 6:
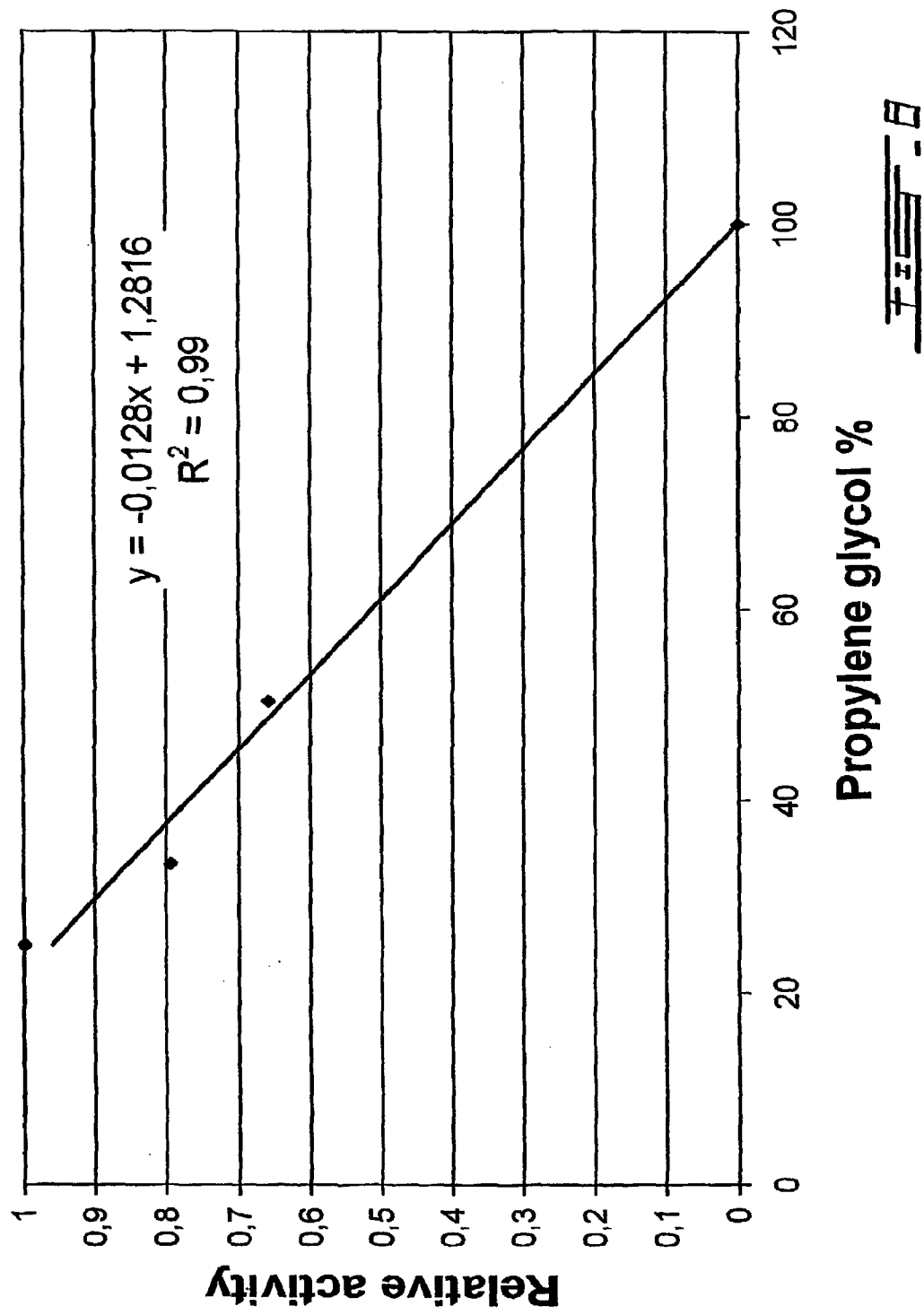

Separation of Plant Fractions:

The homogenization step is followed by a separation step. Thylakoids are separated from cell debris and from soluble components, based on their different sedimentation coefficients. The sedimentation coefficient of thylakoids is superior to that of cell organelles. The thylakoids were centrifuged for 10 minutes at 10,000×g in mobile buckets. A centrifuge force of less than 10,000×g but superior to 3,000 g may be used, adjusting the centrifugation time accordingly (FIG. 7). The optimal handiness for the thylakoids pellets was obtained at 10000-12000×g for 10 minutes. Any other speed and time achieving equivalent results may be adopted. Different speed and time are contemplated in a scaling up process. During sedimentation, the thylakoids pass through a filter corresponding to this equation:

$0.002 \leq X \leq 0.2$ wherein X is calculated by multiplying the opening per the wire diameter (all in millimeters). The cell debris and membranes are stopped by this filter in a superior portion of a centrifugation tube. Thus, the bottom pellets comprising the thylakoids are easily recovered and a pellet may be used immediately or may be further fractionated or stabilized for any future use. Of course, any other method of separation achieving the same purpose of isolating thylakoids could be used. For example, on a density gradient like a sucrose gradient could be used. Any chromatographic or affinity medium and method could be also used. Referring to the above specific method, it is conceivable that the gross and fine separation would not be achieved in one step in a large scale process. Therefore, a gross purification could be made first on a press or a filter and the fine separation of thylakoids and the liquid phase would be achieved in a later step.

Stabilization:

The separation step is normally followed by a stabilization step. This step allows withdrawal of electron donors such as water molecules that are bound or non-bound to membranes, and this for eliminating the activator of the PSII system. The fractions are recovered and are placed in clean vials. Specifically the first, second and third fractions, representing the whole extract, the pellet (thylakoid fraction) and the cell debris/membranes fractions, respectively, are lyophilized. The vials are then submitted to a vacuum and to a low temperature (about −20 to −50° C.), during at least 4 hours. The fractions so lyophilized remain stable for a long time, until water is added thereto. Other stabilizing means could be used. For example, a plurality of surfactants have been used to verify their capacity to chase water without destroying the structure of the thylakoids. These solvents are the following: Triton X-100, PEG, Beta-D-maltoside, glycine, glycerine, glycerol, TWEENs™, SDS, LDS, DMSO, cholate, stearate and propylene glycol have been used.

Propylene glycol has been preferred and would advantageously replace lyophilization as a stabilizer. Not only propylene glycol provides an inactive quiescent thylakoid preparation (functional and fully activable upon water addition, see FIG. 8), but it also stabilize the thylakoids upon hydration by helping solubilizing the same. Upon hydration, thylakoids normally form a suspension; in the presence of 100% propylene glycol, thylakoids form a solution having of limit of solubility of 100 mg/mL solution. This solution may be diluted with water for activation. This solvent is also non toxic.

Optional Fractionation:

The thylakoid membranes could further be fractionated into sub-fractions. For example, it could be envisaged to separate reactional centers or photosystems, light harvesting complexes, cytochrome complexes, particular pigments (chlorophylls, carotenoids), plastoquinones, non-photosynthetic components (cell nuclei), or mitochondria.

Thylakoid Integrity and Activity:

The extract comprises substantially pure thylakoids (>90%); they are photosynthetically activable; they are stable; and the extract is controllable. The photosynthetic activity has been evaluated with different techniques: the oxygen release (Schlodder et al. 1999), the photoreduction of 2,6 dichlorophenol indophenol (DCPIP) (Behera et al. 1983) and the fluorescence (Maxwell et al. 2000). Moreover, the integrity of the thylakoids has been evaluated with a technique which measures a continuous electric current: any disorganization should be detected by any variation in this electric current. The current is measured from PSII to the coupling factor, which indicates that the thylakoids contain the main subunits listed above and that they are functional.

When a green light was used in the working conditions, the pigments were stabilized in their fundamental state ($F_0$), thus, permitting the optimization and synchronization of any desired effect. The stabilization is possible because of the withdrawal of the primary electron donor. The stability measured by the photosynthetic activity (absent during quiescent state and present upon activation with an electron donor) and the concentration in chlorophylls and carotenoids, persist for several months after extraction. The ratio chlorophylls/carotenoids is also extremely important for the activity of the complex and to maximize the absorption and dissipation of energy.

The extracts are easily detectable because of their natural fluorescence. No toxic product, solvent, detergent or conservation agent has been added to the above thylakoids, preserving to the product all its original nature. The extracts are indeed edible. Even when propylene glycol is used to stabilize the thylakoids, this solvent is harmless because its oxidation yields pyruvic and acetic acids. This solvent is currently used as a food emulsifier, which means that it has surfactant properties (however, non deleterious to the integrity of the thylakoids). It further has an inhibitory activity against fermentation and mold growth. Therefore, this solvent may be used at any step in the process, mixed with water during homogenization, and not mixed with water after step c) (separation step).

The extracts may be presented under a solid form, dry or humid, or in a liquid form. The extracts are poorly soluble in water although they rehydrate easily but they resuspend completely in propylene glycol. Thylakoids are reactivated upon rehydration. It is therefore envisageable that a composition comprising solubilized thylakoids is used; when contacted with an aqueous medium, the thylakoids activate.

Byproducts:

Although the thylakoids are the products that have received the primary attention in the above procedure, the other plant constituents that are separated from the thylakoids will also be recovered for their commercial value. The liquid phase fraction and the cell debris/membrane fraction may be easily taken as starting material to isolate any plant molecule of interest. The latter fraction may be reextracted to increase the yield in thylakoids that are recovered per plant unit. It is contemplated that the components of other fractions would have a superior quality when compared to any corresponding components obtained from the processes of the prior art. Because the formation of damaging ROS is prevented or because already formed ROS are captured by the thylakoids prepared in accordance with the present process, it is envisageable that any other plant constituents sensitive to ROS will also benefit from the present process. Indeed, the other constituents that would be normally prone to degrade upon oxidation will be preserved by eliminating a noxious source of degradation. Thus, any plant constituents such as sugars, proteins, lipids, vitamins, minerals and hormones can be separately obtained by fractionating, for example, the liquid phase obtained from the above process, which constituents would have a greater specific activity than usual. In addition to this, a proper conditioning step may enrich the extracts in constituents of interest.

After verifying that the extracts were functional, the next step was to verify their scavenger activity towards ROS.

The Use of Thylakoids as Antioxidants:

Antioxidants are compounds that interact with ROS (such as oxygen singlet, hydrogen peroxide, superoxide anions and hydroxyl radicals). In order to form innocuous degradation products, active oxygen forms degrade or inactivate other molecules and, potentially cause mutations, cancer or inflammation. They may further participate into aging. The antioxidant molecules of the present extracts are the following: chlorophylls, carotenoids and vitamins (B, C, E, K, . . . ), cytochromes and anthocyanins. The thylakoids are particularly performing antioxidants because their physical organization makes the carotenoids capable of capturing singlet oxygen in their chlorophyll protective role. The quenching effect has both a high efficacy and a relatively long duration because the carotenoids dissipate their energy as heat and become ready to accept again the energy coming from triplet chlorophylls. The thylakoids are therefore outstanding in the field of antioxidants; because of their capacity to regenerate their functional state, the organization of the pigments will permit a sustained anti-oxidative activity.

The thylakoids of this invention will hereinbelow be referred to as FRTS/1 constitute a bioactive molecular complex extracted from plant biomass. The functional anti-oxidative activity of FRTS/1 is based on the redox potential of the molecular complexes of thylakoids wherein the tridimensional structure and the natural distance between its different pigments and molecules is preserved. The antioxidant is an indication of an optimal structure and of an optimal composition of matter.

Quantification of Proteins by Fluorescamine Method

The protein concentration in a stabilized extract is: 0.42-0.65 g/g of extract.

Antioxidative Function of the Thylakoids

A—Principal Reaction Pathway in Radical-induced Lipid Oxidation:

Nature employs antioxidants to prevent the oxidation of biomolecules such as proteins, DNA, lipids, etc. The peroxidation of lipids is a particularly ubiquitous and damaging process in living organisms. Peroxyl radicals (ROO.) are important radicals in biological systems because they are able to initiate lipid peroxidation and they are intermediates in many different oxidation processes of biological important molecules.

Initiation (1)

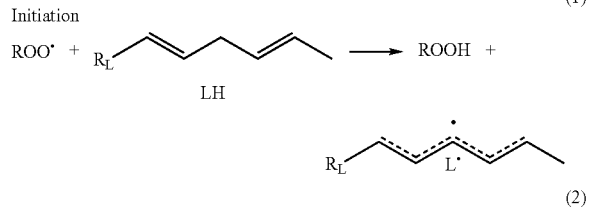

Propagation (2)

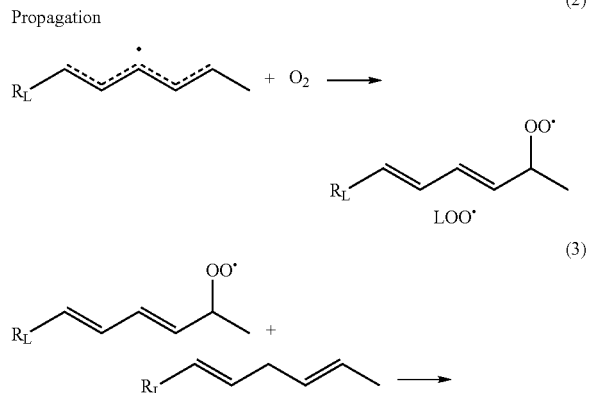

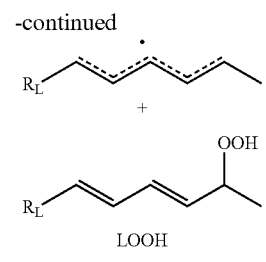

LOOH ($\lambda_{max}$ = 234 nm)

The peroxidation of unsaturated lipid moieties (reactions 1-3) causes changes in their structure which eventually changes the physical properties of biological membranes. During the lipid peroxidation a conjugated diene group is formed (see LOOH in reaction 3) which has an UV/Vis absorption maximum at $\lambda_{max}$=234 nm ($\epsilon$=29,500 $M^{-1}cm^{-1}$) and this allows a quantification of the oxidation product formed. To obtain quantitative data the lipid peroxidation has to be initiated in a controlled manner (reaction 1). Often azo initiators, which produce a well-defined flux of ROO. in aqueous, aerated solution, are employed to study lipid oxidation in in vitro experiments. The most commonly used water-soluble azo initiator is AAPH (sometimes called ABAP; reaction 4).

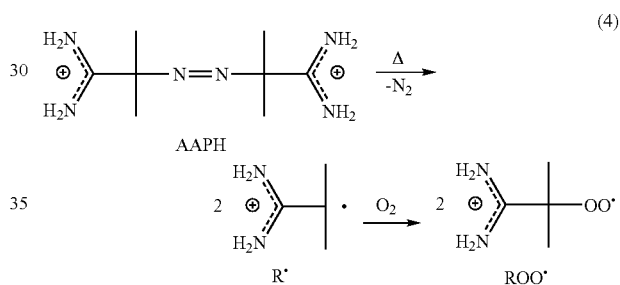

(4)

The decomposition rate of AAPH at 37° C. is k=1.3×10$^{-6}$ $M^{-1}$ $s^{-1}$ and the efficiency for ROO. formation is 50%, i.e. 1 mol AAPH yields 1 mol of ROO.. This method of ROO. generation allows the calculation of the exact amount of ROO. formed during any time period.

The most intensively studied antioxidant is Vitamin E and the most active compound of the Vitamin E family is α-tocopherol (α-TocH). It is a radical chain breaking antioxidant which can trap two peroxyl radicals yielding only non-radical products and thereby preventing lipid peroxidation (reactions 5 and 6).

ROO.+TocH→ROOH+Toc. (5)

ROO.+Toc.→non-radical products (6)

The tocopheroxyl radical (Toc.) formed in reaction 5 is a relatively unreactive radical which normally cannot propagate the radical oxidation chain reaction. As soon as all TocH is consumed the lipid peroxidation occurs as if no antioxidant is present.

Carotenoids (Car) are the most likely "antioxidants" in FRTS/1 because chloroplasts utilize carotenoids such as carotenes and xanthophylls for their exciton transport chain. There are several pathways for reaction of carotenoids with ROS possible and the overall behavior of them ranges from antioxidant activity all the way to being effectiveless with respect to lipid peroxidation inhibition. The experimental results obtained are depending on the reaction conditions employed. Possible reactions of carotenoids with ROO. are:

$$ROO \cdot + Car \rightarrow [Car\text{-}OOR]. \quad (7)$$

$$[Car\text{-}OOR] \cdot + ROO \cdot \rightarrow ROO\text{-}Car\text{-}OOR \quad (8)$$

$$[Car\text{-}OOR] \cdot + O_2 \leftrightarrows \cdot OO\text{-}Car\text{-}OOR \quad (9)$$

$$ROO \cdot + Car \rightarrow ROO^- + Car \cdot^+ \quad (10)$$

$$2Car \cdot^+ \leftrightarrows Car + Car^{2+} \quad (11)$$

$$ROO \cdot + Car \rightarrow ROOH + Car \cdot \quad (12)$$

$$Car \cdot + O_2 \leftrightarrows CarOO \cdot \quad (13)$$

$$ROO \cdot + Car \cdot \rightarrow Car\text{-}OOR \quad (14)$$

Some reactions lead to the formation of non-radical products (reactions 7+8, 10+11, 12+14) which would result in an overall antioxidant behavior of a carotenoid. Other reactions are generating peroxyl radicals (reactions 9 and 13) which can be involved in the propagation of lipid peroxidation. The overall behavior of carotenoids cannot be obviously predicted due to the various possible reaction pathways.

Depending on possible reaction pathways of the antioxidant used the concentration time profiles of the detected LOOH display certain characteristics. By using an azo initiator as peroxyl radical source the amount of ROO. generated can be calculated and it is possible to determine the amount of lipids oxidized from the 234 nm absorption of the conjugated diene moiety. Also the amount of ROO. trapped during the lag phase can be determined.

A process within the FRTS/1 might "restore" its "original" antioxidative properties. A possible mechanism for such a behavior might be an electron transfer rather than a radical trapping process (see reactions 15 and 16), e.g.:

$$ROO \cdot + PCPE \xrightarrow{H^+} ROOH + PCPE \cdot^+ \quad (15)$$

$$PCPE \cdot^+ + S \longrightarrow PCPE + S \cdot^+ \quad (16)$$
$$\downarrow$$
$$\text{further reactions}$$

S: Substrate

Figure 9:
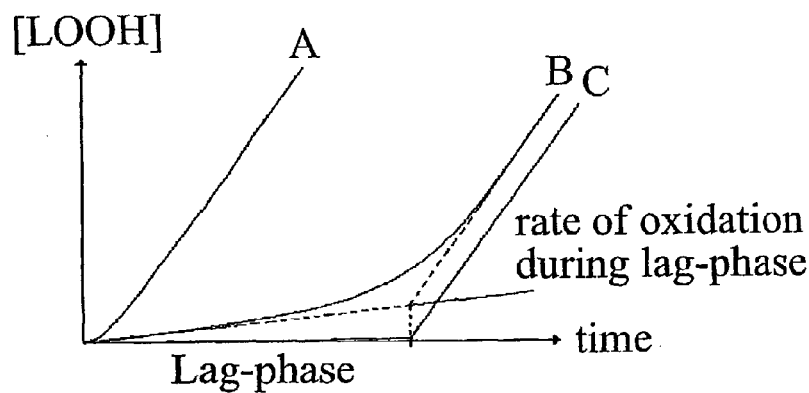
FIG. 9 shows oxidation curves. Curve A represents a lipid oxidation without any antioxidant; curve B shows lipid oxidation in the presence of an anti-oxidant which "allows" some lipid oxidation; curve C represents lipid oxidation in the presence of an efficient radical chain breaking antioxidant, such as vitamin E.

The concentration/time profiles of the lipid oxidation in the presence of FRTS/1 will allow examining this hypothesis. From the duration of a possible lag phase during lipid peroxidation experiments (FIG. 9) the amount of "trapped" radicals can be calculated. This will allow to draw conclusion to which extend FRTS/1 is able to inactivate peroxyl radicals. However, it has to be born in mind that the described possible regeneration of the antioxidative properties can be only effective as long as FRTS/1 is still intact and able to perform its "original" activity. Overall the experiments will eventually provide quantitative data for the antioxidative capacity of FRTS/1 (see FIG. 10 for an example of the antioxidative kinetics of FRTS/1 in comparison of Trolox). When β-carotene was compared to Trolox, the former was an antioxidant but with no lag phase typical of antioxidants.

Since lipids are the main components of the cell membrane, lipoproteins and other membrane structures in living organisms, in the present study PLPC-FRTS/1 (1-palmmitoyl-2-linoleoyl-sn-glycero-3-phosphatidylcholine) micelles were used as a substrate for the standard oxidation assay. Oxidation of PLPC-FRTS/1 induced by peroxyl radicals generated from the initiator Azo compound 2,2' Azobis-(2-amidinopropane)dihydrochloride (AAPH) results in oxidation of the linoleic acid moiety to the corresponding hydroperoxide together with the formation of a conjugated diem system with an absorption maximum at 234 nm.

Preparation of PLPC(l-palmmitoyl-2-linoleoyl-sn-glycero-3-phosphatidylcholine) Micelles:

170 μL of a 25 mg/mL solution of PLPC-FRTS/1 in CHCl₃ (Avanti Polar Lipids) was evaporated to dryness under a stream of $N_2$. Phosphate buffered saline (PBS) (281 μL) which had been previously treated with Chelex® to remove metal ions was added to the PLPC-FRTS/1 and the mixture was vortexed 2 min. Aqueous Chelex® treated sodium cholate 109 μL, 30 mg/mL, (Aldrich Chemical Company Inc., Milwaukee, Wis., U.S.A) was added to the mixture and vortexed 2 min. The mixture was passed 20 times through a polycarbonate membrane (pore size 100 nm) in order to homogenize the size of the micelles.

FRTS/1 was dissolved in CHCl₃ (12 mg/mL) and I ml of this solution was mixed with 6 mL of PLPC-FRTS/1 (25 mg/mL) to obtain a final concentration of PC-FRTS/1 of 6 mg/ml. Micelles were prepared as described above. Azo initiator (AAPH) was used at a concentration of 5 mg/mL in PBS.

Standardization:

Initial experiments were performed using FRTS/1 in a dehydrated form, to standardize the concentration of micelles, azo initiators and wavelengths. Optimal absorbance was at 234 nm.

Two preliminary experiments were run with 100 μl micelle solution prepared from PLPC-FRTS/1 and PLPC-FRTS/1+ FRTS/1 in 3 mL of PBS with two dilutions (10 μl and 20 μl) of 5 mg/mL solution of azo-initiator for 10 h at 37° C. at wavelength 234 nm on a Cary 3 UV-Visible spectrophotometer from Varian. The background absorption due to the PC-FRTS/1 at 234 nm was too high under these reaction conditions.

EXPERIMENTS

Based on the results obtained from the above experiments, it was decided to use further diluted solutions of the FRTS/1 (final concentrations of FRTS/1 were 6.7 μg). As negative control, the FRTS/1 was incorporated into micelles made from 1,2-Dimyristoyl-sn-glycero-3-phosphatydylcholine (DMPC) a compound which is resistant to oxidation mediated by peroxyl radicals derived from AAPH. Micelles were prepared from 15.937 mg of DMPC-FRTS/1 (stock solution 25 mg/ml) in 0.6375 mL of PBS+1.053 mL of PBS+0.408 mL of Sodium cholate+0.2435 mL of FRTS/1 solution in CHCl₃ (2 mg/mL) as described above. The following experiments were therefore conducted:

3 mL of PBS+100 μl of PLPC-FRTS/1 micelles+10 μl of azo-initiator 3 mL of PBS+100 μl of PLPC-FRTS/1 micelles+20 μl of azo-initiator 3 mL of PBS+100 μl of DMPC+FRTS/1+10 μL of azo-initiator 3 mL of PBS+100 μl of DMPC+FRTS/1 20 μL of azo-initiator 3 mL of PBS+10 μl of azo-initiator 3 mL of PBS+20 μl of azo-initiator The reactions were monitored on a spectrophotometer at 37° C. for 10 h.

Conclusion

These results show that the maximum OD (at 234 nm wavelength) of PLPC-FRTS/1 micelles containing FRTS/1 at 0.3 mg/mL was 0.25 after 180 min while OD of PLPC-FRTS/1 micelles without FRTS/1 was 3.2 after the same period of time. The results indicate that the FRTS/1 undoubtedly demonstrate antioxidative properties.

Antioxidant Properties of FRTS/1 Solution in Comparison of Vitamin E

Figure 10:
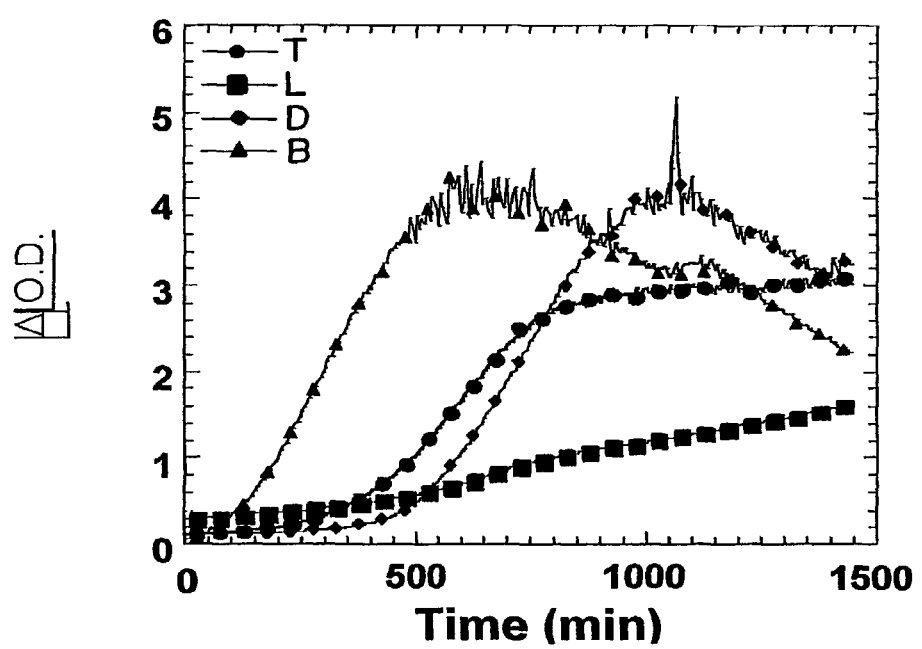
FIG. 10 illustrates the oxidation kinetics of lipids PLPC, wherein B stands for lipids without the extract of this invention, D stands for lipids in the presence of Trolox, L stands for lipids in the presence of an active extract made in accordance with this invention and T stands for lipids in the presence of lipids treated with an inactive extract.

Lower concentrations of antioxidants was used to compare the antioxidative properties of FRTS/1 and Trolox, a water soluble analog of Vitamin E (0.3 mg/mL in PBS). The following samples were run on spectrophotometer for 10 h at 37° C.
1. 3000 µL of PBS+10 µL of azo-initiator.
2. 3000 µL of PBS+100 µL of PLPC micelles+10 µL of azo-initiator.
3. 2998 µL of PBS+2 µL of antioxidant (0.5 mg/mL aqueous solution)+100 µL of PLPC micelles+10 µL of azo-initiator
4. 2995 µL of PBS+5 µL of antioxidant (0.5 mg/mL aqueous solution)+100 µL of PLPC micelles+10 µL of azo-initiator
5. 2990 µL of PBS+10 µL of antioxidant (0.5 mg/mL aqueous solution)+100 µL of PLPC micelles+10 µL of azo-initiator
6. 2980 µL of PBS+20 µL of antioxidant (0.5 mg/mL aqueous solution)+100 µL of PLPC micelles+10 µL of azo-initiator
7. 2990 µL of PBS+10 µL of Trolox+100 µL of PLPC micelles+10 µL of azo-initiator
8. 2980 µL of PBS+20 µL of Trolox+100 µL of PLPC micelles+10 µL of azo-initiator
9. 2970 µL of PBS+30 µL of Trolox+100 µL of PLPC micelles+10 µL of azo-initiator FIG. 10 shows a more sustained activity for FRTS/1 than for Trolox.

Protection Mechanism:

Radical Oxygen Species (ROS) readily interact with cellular macromolecules and structures, resulting in membrane permeability changes, activation of proteases and nucleases, and altered gene expression (Yu, 1994; Schiaffonati and Tiberio, 1997). It is well known that these cellular changes induced by ROS lead to apoptotic cell death. We attempted:
To evaluate the antioxidative properties of FRTS/I; and
To determine the action mode of FRTS/1 as an antioxidant.
IMR-32 cells constitute a good model for evaluating the antioxidant potency of our extract. These cells are neuroblastoma cells that are sensitive to an oxidative stress which provokes apoptosis.

Experiment 1

Standardization of Experimental Conditions

Selection of Cell Culture

Human neuroblastoma cell line (IMR-32), which is known to respond to oxidative stress by apoptosis (Kim et al, 1999), was used as an in vitro cell model. IMR32 cells are particularly sensitive to ROS and other toxicants because their p53 gene product is sequestered in the cytoplasm. The sequestration renders the p53 inactive although the gene is not mutated.

Selection of ROS Inducer

Tert-butyl hydroperoxide (TBHP) was used as an oxidative stress-inducing agent. TBHP does not have any neuron specificity in contrast to oxidative stress induced by MPTP in dopaminergic neurons. This will allow comparisons if studies relative to more generalized oxidative stress conditions (like the ones found in many neurodegenerative diseases) have to be performed on different cells phenotypes.

A. Determination of Optimal Dosage of TBHP to Induce Apoptosis on IMR-32 Cells Culture Experiments were done using 1000 IMR-32 cells per well, for I hour of incubation. TBHP 50, 75 and 100 µM produced 78%, 87% and 87% apoptosis. TBHP 50 µM was selected to induce apoptosis in the other experiments.

B. Dosage of FRTS/1

Different dilutions were used on IMR-32 cells along with TBHP. A mother solution 1:10 was constituted, starting from the lyophilized thylakoid fraction, in propylene glycol. Unless otherwise specified, the mentioned dilutions are dilutions of this mother solution. The protection conferred by FRTS/1 was 28%, 35% and 75% at dilutions 1:10, 1:100 and 1:1000, respectively. The latter dilution was adopted for further experimentation.

1. Cell Culture

IMR-32 Cells were grown in MEM supplemented with 10% FBS at 37° C. in a humidified atmosphere of 95% air and 5% $CO_2$. The cells were seeded at a density of $1\times10^4$ cells/ T25 Falcon tissue culture flasks and subcultured twice weekly. 48 h old cultures were used in all the experiments. 1000 cells were plated per well in the first experiments, the number was increased to 3000 afterwards as indicated in the tables.

2. Oxidative Stress in vitro Protocol 1000 or 3000 cells/well/100 uL were seeded in 96 well (Linbro flat bottom) plates in all the wells except well No. 12 of all the rows. After 24 h the cells were washed 2 times with 250 ul of PBS (pH 7.2) and 32 wells each were treated respectively with 100 and 200 uM solutions of TBHP (70% aqueous solution from Sigma Chemical Company) for 1 h. After 1 h the cells were gently washed 2 times with PBS before adding fresh growth medium. After 24 h the cell survival was assayed by a sensitive fluorimetric assay based on DNA binding fluorescent dye Hoechst by the following procedure. The test measures the total DNA of the population, a measurement which closely correlates with cell number. The medium was aspirated by gentle suction. Cells were rinsed with 250 ul PBS. PBS was aspirated with gentle suction. The rinse step was repeated. 100 uL lysis buffer (0.02% SDS in 1×SSC) was added in every well except the ones for DNA standard and Blank in row 12. The plate was incubated at 37° C. for 1 h with occasional swirling. 100 uL of 40 ug/mL of DNA was added to the DNA wells and 100 uL of 1×SSC buffer was added to the wells that were treated as Blank. 100 uL of 40 ug/ml of Hoechst 33258 in 1×SSC buffer was added to every well, and the plate was covered with Aluminum foil to protect it from light. The plate was agitated gently for 5 minutes and fluorescence was read at excitation wavelength 355 nm and emission wavelength 460 nm.

3. Calculations

CT untreated=100%: survival after TBHP: 42%, dead cells: 100−42=58%; population size after PC: 88% difference from CT: 100−88=12% Expected population size after TBHP+PC: 100−58−12=30%. Recovered survival: 60% Survival gain in %: 60−30=30 Protection exerted: 30:60×100=50%

4. Estimation of Cytotoxicity by LDH Assay:

For this experiment IMR-32 cells were grown in MEM medium without I-Glutamine, Phenolphtaleine and sodium pyruvate 3000 IMR-32 cell/well seeded in 96 well plates. 24 hours after the oxidative stress, the cells were washed 2 times with PBS and two rows each were treated with 1:1000 and 1:10000 PC-FRTS/1 for 1 hat 37° C. After 1 hour the cells were washed with PBS two times and PBS was replaced with the growth medium. Two rows each were treated with 1:1000 and 1:10000 PC-FRTS/1 while two rows each we treated with 25 and 50 uM TBHP respectively. Two rows were left untreated as Control. The LDH activity was measured by Lactate Dehydrogenase Assay Kit provided by Sigma Diagnostics. The calorimetric assay measures the residual pyruvate (substrate of the enzymatic reaction). The basal activity present in the medium alone (in the absence of Cells) was considered 0% and was systematically subtracted from each experimental value. Control untreated cells in two rows were lysed with Triton X-100 (0.02%) and were treated as samples with 100% LDH release.

Initial two experiments were done to standardize the procedure, number of cells used wave length for optimum absorbance, optimum pyruvate substrate to be used. It was established that 3000 cells/well, 0.4 ml of pyruvate, spectrophotometer readings at 440 nm were standards.

FRTS/1 was used as pre-treatment, co-treatment and post-treatment with the oxidative insult.

Pre-Treatment.

The cells were pre-treated with FRTS/1 for 2 h before exposure to TBHP doses.

|  | TBHP | |
| --- | --- | --- |
|  | 25 uM | 50 uM |
| Cell damages TBHP/CT | 58% | 70% |
| FRTS/1 1:1000 decrease | 12% | 12% |
| Total expected decrease | 70% | 82% |
| Expected survival | 30% | 18% |
| Survival TBHP + PC/CT | 60% | 53% |
| Protection exerted by PC | 50% | 77% |

Co-Treatment

The cells were treated simultaneously with FRTS/1 and TBHP for 1 hour.

|  | TBHP | |
| --- | --- | --- |
|  | 25 uM | 50 uM |
| Cell damages TBHP/CT | 39% | 67% |
| FRTS/1 1:1000 decrease | 7% | 7% |
| Total expected decrease | 46% | 74% |
| Expected survival | 54% | 26% |
| Survival TBHP + PC/CT | 83% | 62% |
| Protection exerted by PC | 35% | 62% |

Post Treatment

The cells were treated with 3 doses of FRTS/1, 1 hour after to have been exposed to TBHP doses.

|  | TBHP | |
| --- | --- | --- |
|  | 25 uM | 50 uM |
| Cell damages TBHP/CT | 38% | 66% |
| FRTS/1 decrease | 7% | 7% |
| Total expected decrease | 46% | 74% |
| Expected survival | 54% | 26% |
| Survival TBHP + PC-CT | 71% | 72% |
| Protection exerted by PC | 23% | 62% |

The <<Cell damages TBHP/CT>> represents the damages caused by the oxidant calculated as a percentage from the survival of untreated controls. The <<FRTS/1 decrease>> refers to the difference in population size in controls and FRTS/1 exposed cells. The <<Total expected decreases>> sums the difference in population size due to TBHP and FRTS/1 exposure individually. The <<Expected survival>> is 100-total expected decrease. The <<survival TBHP+PC/CT>> is the actual survival in the presence of FRTS/1 diluted 1:1000. The <<protection exerted by PC>> is calculated as reported above.

In the pre-treatment experiment, the effect of FRTS/1 is enhanced when compared to protection exerted by a post treatment (compare 50% to 23% and 77% to 62%). It strongly suggests that the protective effect of PC-FRTS/1 is exerted through its antioxidant properties. At low dose (25 uM), the protection against the damages caused by the oxidant doubles.

Clearly, the efficacy of PC-FRTS/1 is confirmed as a preventive treatment due to its antioxidant properties.

The antioxidant properties of FRTS/1 are confirmed in the co-treatment experiment. The efficiency of the product is similar to the one reported for post-treatment at the highest dose of oxidant and intermediate to the one obtained following pre- and post-treatment, respectively.

FRTS/1 exerts its protection against apoptosis caused by TBHP during the course of TBHP damages.

The strong antioxidant properties of FRTS/1 are confirmed via its protective effect on ROS generated in the IMR-32 cells by the oxidant TBHP. Under our standardized conditions, the protective effect averages 62%.

Figure 11A:
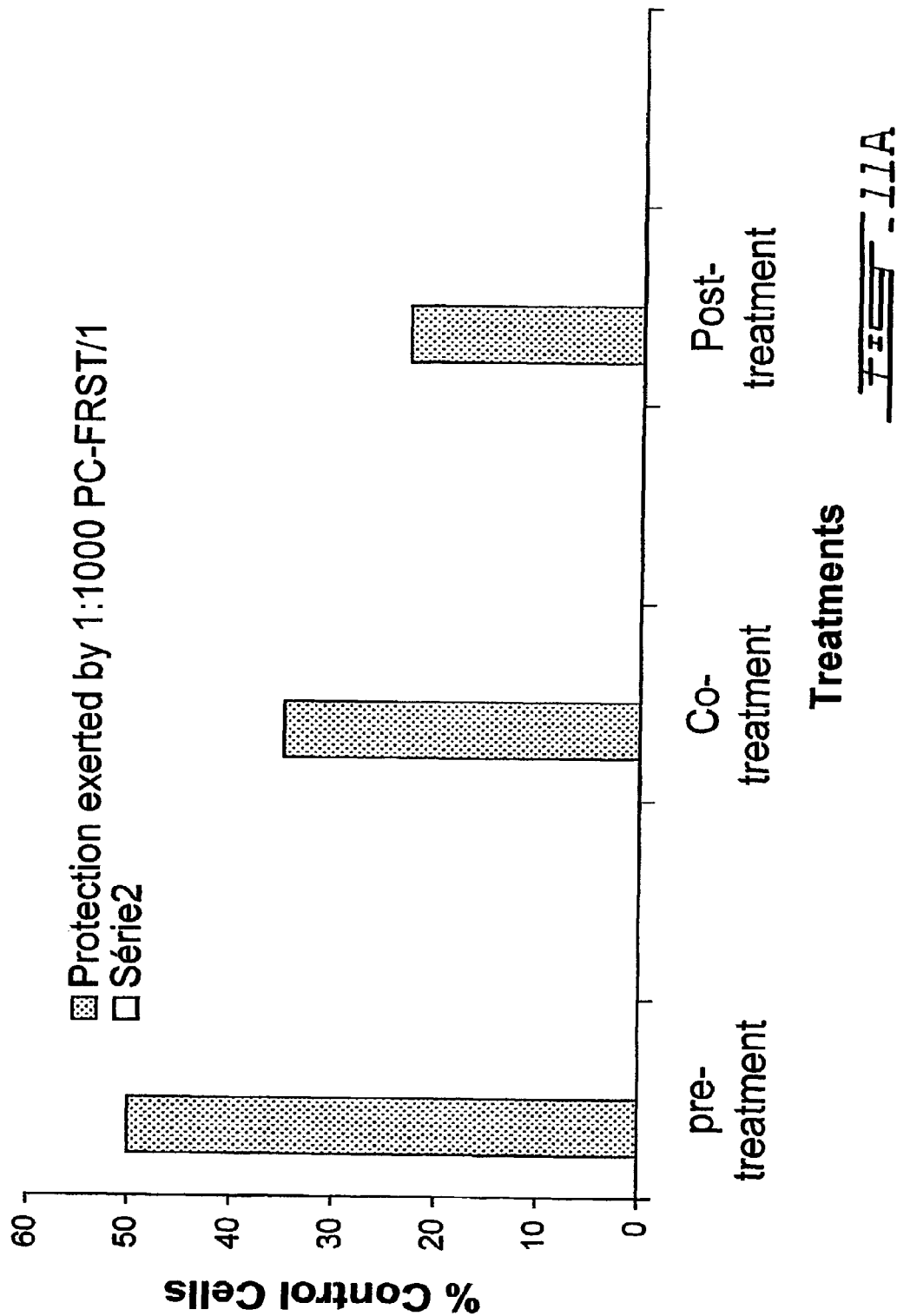
FIG. 11a): 25 µM.

The antioxidant effect occurs on pre, co- and post-treatment. (FIGS. 11a and b)

Figure 12A:
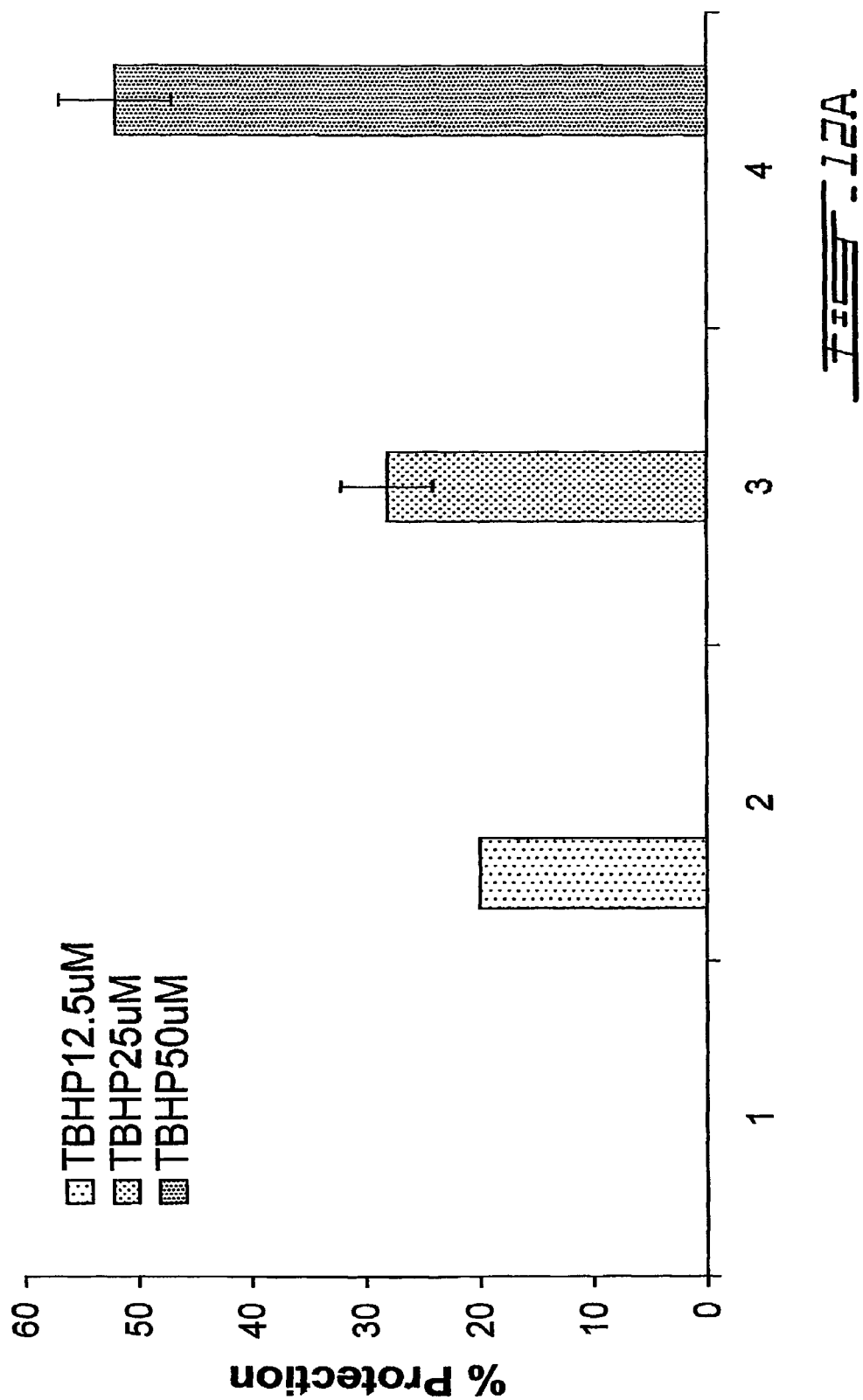
FIG. 12a): dilution 1:1000.
Figure 12B:
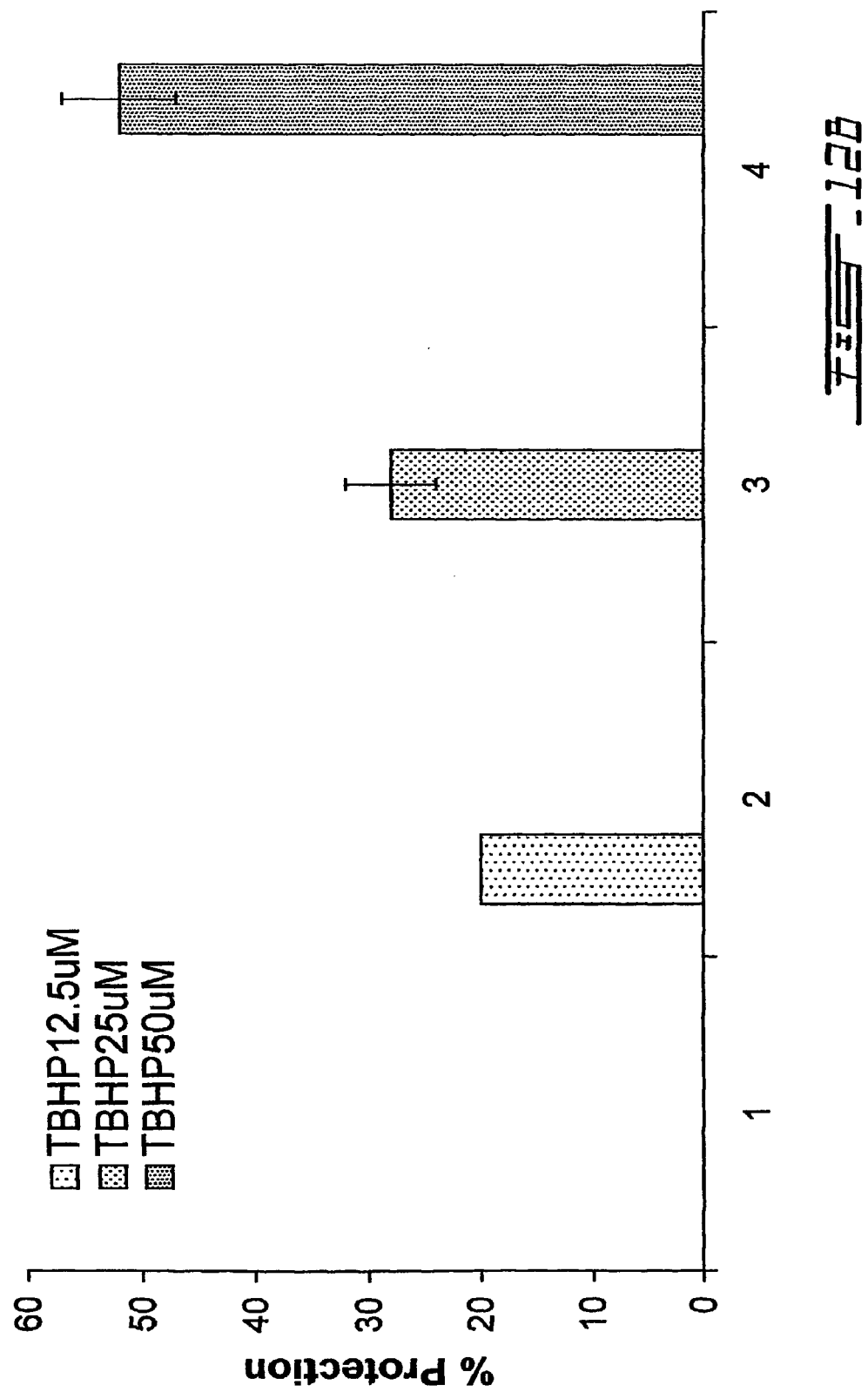
FIG. 12b): dilution 1:10000.
Figure 13:
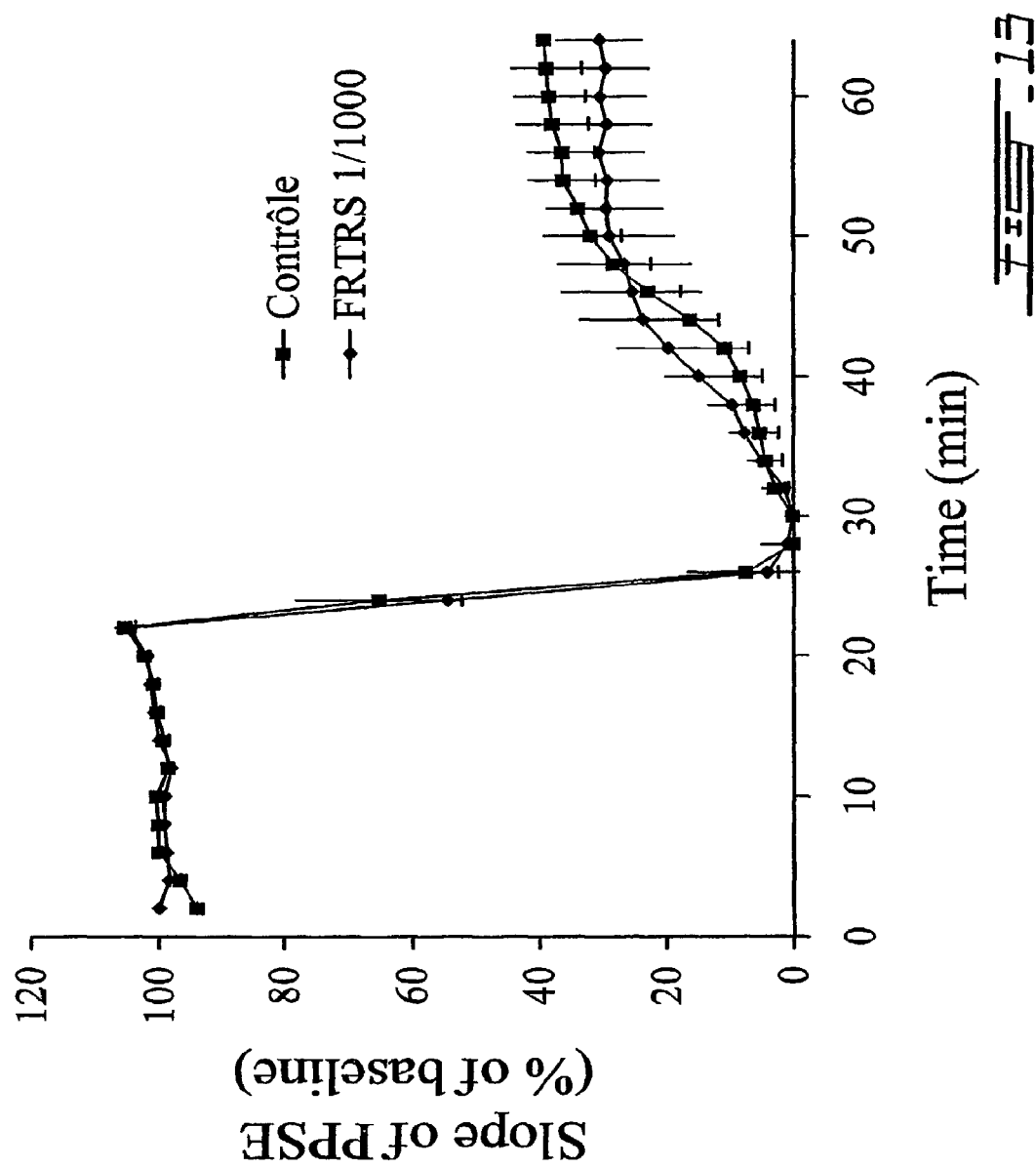
FIG. 13 illustrates the behaviour of brain hyppocampus slices to a 120 sec. epoxia and recovery in the presence of a solution comprising the extract of the present invention or not (control).

The more the oxidative damages caused by TBHP on the IMR32 cells (as TBHP dosage increases), the more the protection exerted by FRTS/1. This is independent from the concentration of FRTS/1 since it shows at 1/1000 as well as at 1/10,000 dilutions (illustrated in FIGS. 12A and 12B respectively and). These results show the dynamism of the present extract.

The fact that the protection increases with increasing damages indicates that the mechanism of action of FRTS/1 may differ from that of conventional antioxidants as indicated in the studies relative to the chemistry of the reaction:

1) the protective effect exerted by FRTS/1 lasts longer
2) The vitamin E and its analogs are used up at given concentrations, while they exert their antioxidant effect. It does not seem to be the case with FRTS/1 as illustrated by the above chemical reactions shown in above.

The correlation between extent of oxidative damages and protection by PC-FRST/1 is a unique property shown by this antioxidant.

Increasing the cell density from 1000 to 3000, obviously decreases the dose of product that each cell receives. This is a well-known effect in toxicology and pharmacology. The protection exerted by FRTS/1 remains excellent even when the number of cells to be protected triple. The effect is reproducible.

Estimation of Apoptosis in IMR32 Cells by Lactic Deshydrogenase (LDH) Assay:

The classical LDH assay measures the release of the LDH enzyme by apoptotic cells. The assay used in the present study measures the residual level of enzyme substrate (pyruvate) using a calorimetric reaction. The more the substrate in the medium, the less enzyme released. Medium cells was taken as 0% enzyme activity released, and lysed cells in the medium as 100% released. The table values are calculated from these two parameters.

Level of Apoptosis Measured by Release of LDH by the Damaged Cells:

|  | PC-FRTS/1 doses | | | |
| --- | --- | --- | --- | --- |
|  | 1:1000 | | 1:10 000 | |
| TBHP concentrations | 25 uM | 50 uM | 25 uM | 50 uM |
| LDH release/TBHP | 64% | 92% | 64% | 92% |
| LDH release/PC | 32% | 32% | 0% | 0% |
| Expected LDH releases | 96% | 124% | 64% | 92% |
| Observed LDH TBHP + FRTS/1 Release | 49% | 73% | 30% | 66% |

The total release of LDH by TBHP plus FRTS/1 individual exposures was compared to the observed LDH activity (last row).

The protective effect of FRTS/1 is obvious. A post treatment by FRTS/1 protects effectively the IMR-32 cells against apoptosis induced by the ROS generated by TBHP.

Conclusion

FRTS/1 compound exhibits potent antioxidant properties as assessed by chemical assays.

These highly efficient antioxidant protective effects are also exhibited in a biological in vitro assay:

FRTS/1 antioxidant properties demonstrated chemically are confirmed biologically;

FRTS/1 exhibits highly protective effects against ROS damages causing apoptosis in IMR-32 cells following TBHP exposure;

FRTS/1 presents the unique property to be dynamic so to exert higher protective effect as oxidative damages increase (the higher the damages by ROS, the higher the protection by FRTS/1);

FRTS/1 exhibits a long lasting (hours) anti-oxidative effect which shows a great level of stability and/or a capacity to regenerate, which is unique to this antioxidant;

FRTS/1 is efficient at doses that are not toxic.

Interaction Between Cells:

To be an effective therapeutic medication, the present extract must fulfill at least some characteristics. Amongst these, the extract not be toxic, immunogenic or hinder the normal tissue function, particularly the oxygen and carbon dioxide erythrocyte transport.

The extract should not stick to erythrocytes, although they should disperse in the recipient body to target a tissue or organ to be treated. We have verified if macrophages, which are first line defence cells do not destroy the present extract. Macrophagic mode of destruction is normally production of free radicals which destroy big particles before phagocytosis. Upon phagocytosis, macrophages produce cytokines which are molecules signaling the presence of any intruder or the malfunctioning of a tissue or cell. Cytokines are molecules sent to other cells, signalling the presence of intruders or of a malfunctioning of a tissue. The cells responding to cytokines are cells like fibroblasts, endothelial cells, macrophages, lymphocytes, neutrophils and eosinophils. These cells are involved in the process of destruction and/or reconstruction of tissues and organs. These processes involve inflammation. If the response is disorganized or if the intruder is continuously present in the organism, the latter suffers of a chronical diseases such as rheumatism, cutaneous irritation, conjunctivitis, alveolitis, asthma, and even cancer. The interaction between cells and FRTS/1 were performed with the FACS technique. This apparatus detect fluorescence of cells (autofluorescence) and also all fluorescent molecules fixed around. FRTS/1 is a autofluorescent complex, so we can quantify interactions without any modification.

Conclusion: FRTS/1 adhere to macrophages (commercial lines: NR-8383 by ATCC) at 37° C. with comparison with mastocytes (positive control, RCMC provided by ATCC). Macrophages phagocyte FRTS/1 (⅓) after 2 hours, which demonstrates that FRTS/1 stays for a rather long period in blood flow. Slow phagocytosis is not a bad news, per se, since another type of beneficial effect could be observed consequent to the cytokin activation ("phase II" effect). Since macrophages phagocyte the extract and since IMR-32 cells appear to allow entrance to the extract into the cytoplasm, it is believed that the extract may enter the cells by endocytosis.

Oxidative Ex Vivo Models

Liver perfusion model and brain perfusion model are good experimental models responsive to an oxidative stress. They were used to demonstrate the protective effect of the extract towards vital organs.

Liver Perfusion Model

A plurality of hepatic functions have been evaluated. The method used to perfuse the liver was described by Drouin et al. 2000 and by Lavoie et al. 2000. Glucose, lactate, ALT and LDH were determined by spectrophotometry, while bile production was simply measured by volumetry. When compared to a control vehicle, there was no deleterious effect observed with the perfusion of the extract. On the contrary, when the potency of the extract to reduce the expression of a stress created by ischemia followed by re-perfusion (I/R), the results were that the extract had a protective effect against oxidative damages induced in the liver.

In this model, the liver is perfused in situ with a controled extracorporeal circulation, which isolates the liver while preserving its vascular bed intact and saving its structural and functional integrity. This model is well documented (Ross 1972) and allows the study of oxidative stress as well as of cell damage (Bailey 2000).

Effect on liver viability is undertaken to evaluate the effect FRTS/1 on liver viability. More specifically, the effect of FRTS/1 on hepatic functions during in situ perfusion is evaluated.

The livers of Sprague-Dawley rats are perfused in situ with a single-pass system in a standard Krebs-Henseleit (K-H) solution. [pH 7.4, $O_2$:$CO_2$ (95%:5%)] The K-H solution is composed of: NaCl (118 mM), KCl (4.8 mM), $KH_2PO_4$ (1.2 mM), $MgSO_4.7H_2O$, $CaCl_2$ (1.5 mM), $NaHCO_3$ (25 mM) and albumin (2% w/v).

Under anesthesia (pentobarbital; 50 mg·$kg^{-1}$ body weight), a laparatomy is performed to expose the portal vein, the inferior vena cava and the biliary channel for canulation. The portal canulation is used as the entrance of the perfusate into the liver and that of the vena cava is used for recovering the perfusate at the liver exit. The nervus vagus is sectioned to isolate the liver from any vasomotor influence. The total surgical procedure is completed within 15 minutes. The time interval between the insertion of a canula into the portal vein and the beginning of the circulation is not more than 3 minutes. The time lapsed between the cardiac arrest caused by the thoracic cage opening and the beginning of the perfusion is not beyond one minute.

The total duration of the perfusion was 60 minutes. During the first 30 minutes, a wash out was performed. During that period, the K-H solution (37° C.), was supplemented with glucose (8 mM), lactate (0.5 mM), alanine (0.2 mM) and glycerol (0.02 mM) was circulated in the liver in an open circuit. Thereafter, the liver was exposed to vehicles only (control), or to FRTS/vehicles (treated FRTS/1 group), for another 30 minutes. The vehicles comprise either saline (1 ml/800 ml perfusate), or 1,3-propanediol (24 ml/800 ml perfusate). FRTS/1 was added to either propanediol (0.06 mg FRTS/ml propanediol:24 ml/800 ml perfusate) or to saline (2 mg FRTS/ml saline: 1 ml/800 ml perfusate). The perfusate flow rate was kept constant at 6 ml/minute/100 g body weight). A small sample of the perfusate was taken at the entrance and at the exit of the liver, for determining the production of the utilization of metabolites.

The concentrations of glucose, lactate, ALT and LDH in the perfusate were determined by photospectrometry using commercial procedure disclosed by Sigma-Aldrich Canada n. 17-UV, No. 735, No. 59-UV and No. DH1240-UV, respectively). The extraction or the production of a substrate by the liver is measured by the differences between the entrance and the exit of a metabolite, multiplied by the perfusate flow rate.

Since the nature of the vehicle did not influence the measured parameters, the results have been combined.

The bile production was similar in both control and treated groups (0.55±0.10 v. 0.62±0.12 mg/min/g liver, in the control and treated group, respectively). During reperfusion, bile production diminished when compared to the pre-ischemia levels in both treated and control groups. Bile production returned to normal levels within 10 minutes after reperfusion.

At the entrance, the glucose concentration was similar in both groups (7.04±0.40 v. 7.24±0.07 mM in control and treated group, respectively). In both groups, the liver has slight tendency to use glucose. The exposure to FRTS/1 has no effect on glucose capture (0.32±0.21 v. 0.39±0.25 µM/min/g liver in control and treated group, respectively). The concentration of lactate at the entrance was also similar in both groups (0.60±0.33 v. 0.50±0.10 mM in control and treated group, respectively). Upon exposure to FRTS, there is a slight tendency in the treated livers to produce lactate (−0.01±0.1 v. 0.40±0.005 µM/min/g liver in the control and treated group, respectively).

Perfusing the liver by itself does not provoke any release of ALT or LDH in the control groups (−0.07±0.14 and 1.79±0.47 µM/min/g, respectively). Treatment with FRTS/1 does not appear to provoke a release of ALT or LDH by the liver (0.57±0.21 and 2.36±1.10 µM/min/g), although there is a slight tendency to increase. When liver were partly perfused before the use of FRTS, there was a progressive increase of the LDH production by the liver (35.57±8.96 µM/min/g).

These preliminary results lead to believe that FRTS/1 has no remarkable effect on the viability of perfused liver. More specifically, treatment with FRTS/1 do not appear to modify the liver functions during a 30 minute perfusion duration, as evaluated by the utilization of glucose, the production of lactate and of bile. There is no apparent structural damage to the hepatocytes, since there is no increase of ALT and LDH.

The above was slightly modified to study the effect of ischemia and reperfusion. The total duration of the perfusion was 105 minutes. The 31$^{st}$ minute constituted a wash out period. During that period, a K-H solution (pH 7.4 and in the presence of $O_2:CO_2$ 95%:5%) was added to glucose 8 mM, lactate 0.5 mM, alanine 0.2 mM and glycerol 0.2 mM. The solution was circulated in an open circuit. Then, the liver was exposed to the extract or to the vehicle: 1,3-propanediol for 15 minutes. The perfusing rate was kept constant at 6 ml per minute per 100 g of body weight (Drouin et al. 2000, Lavoie et al. 2000). The perfusion was stopped for 30 minutes. During this arrest, ischemia developed. Then circulation was re-established for a duration of 30 minutes. The perfusing liquids were taken at the entrance and at the exit of the tested livers, for measuring the production or the use of the evaluated biological markers.

Upon re-perfusion, the bioproduction diminishes compared to the pre-ischemia levels in both control and treated livers. These levels return to normal within 10 minutes after the beginning of the re-perfusion. Control and treated livers release glucose in identical way (10.4±0.7 µM·minute$^{-1}$·g$^{-1}$). Glucose production was however slightly superior after 80 minutes in the treated group, compared to the control organs. Lactate accumulated during ischemia in higher levels in treated livers (5.9±0.5 µM·minute$^{-1}$·g$^{-1}$). when compared to the control organs (4.5±0.1 µM·minute$^{-1}$·g$^{-1}$).

Pre-treatment with the extract decreases the release of ALT (1.09±0.44 mU·minute$^{-1}$·g$^{-1}$ vs. 2.44±0.79 mU·minute$^{-1}$·g$^{-1}$, respectively) during re-perfusion. Pre-treatment with the extract appears to diminish the impact of ischemia for the first 30 minutes of re-perfusion. Ischemia without any pre-treatment with the extract, provokes an increase of LDH (108.7±27.3 mU·minute$^{-1}$·g$^{-1}$) during re-perfusion. Pre-treatment with the extract does not influence LDH in increase (115.9±60.8 mU·minute$^{-1}$·g$^{-1}$)

Potassium and sodium plasmatic concentrations were also measured in both groups. At the beginning of the re-perfusion, the release of potassium in treated group is superior to the control (0.43±0.01 mU·minute$^{-1}$·g$^{-1}$ vs 5.4±0.1 mU·minute$^{-1}$·g$^{-1}$, in control and treated groups, respectively). In the perfusate, at the entrance, the plasmatic concentration of potassium and sodium were similar in both groups. ($K^+$=5.6±0.3 mM and 5.4±0.1 mM in control and treated groups, respectively; $Na^+$=142.2±8.6 mM and 137.2±15.2 mM, in control and treated groups, respectively).

At the beginning of the re-perfusion, the release of sodium was also superior in treated groups when compared to the controls (1.2±1.1 µM·minute$^{-1}$·g$^{-1}$ and 16.5±3.9 µM·minute$^{-1}$·g$^{-1}$, respectively).

Ischemia followed by re-perfusion is characterized with circulatory and metabolic disturbance, and with tissue damage provoked by free-radicals (Lee 2000). This particular model is currently used to evaluate the damage provoked by free radicals in tissues or organs subject to transplantation (Smrekova 2000, Cohen 2000 and Hachimoto 2000). Structural and functional disturbance is occasioned by I/R and are reflected by an increase in the release of enzymes (Bailey 2000, Vollmar 1994 and Perlata 1999), a decrease of bile production (Vollmar 1994) and a depletion of ATP reserve (Hwang 1999 and Amllet 1990). Ischemia may lead to the production of singlet oxygen, peroxide, and superoxide ($O_2^-$., $H_2O_2$, OH.) following the release of metal ions like iron and cupper (Halliwell 1999). This model is therefore a good one for characterizing a protective effect, if any, which would be present in the present extract following a radical insult.

Metabolic changes insuring protection of hepatic cells are affected by pre-treatment with the extract. A radical attack consequent to I/R provoke decrease in ATP cell content, thereby modifying the energetic state of the cell (Peralta 2000, Mallet 1990). Tamarina et al. (1984) suggest that ischemia damages the glycolytic system of a cell, which renders difficult the lactate production. A healthy cell (or a cell under the action of a protecting agent) would protect itself from such a stress by increasing its ATP production via the glycolitic pathway. Sano et al. (1995) proposed that glycolytic activation reduces I/R-induced free-radical formation. Also phosphoenolpyruvate prevents the ATP decrease consequent to I/R (Saiki 1999). Hwang et al. (1999) suggest that a decrease of the ratio $NAD^+/NADH$ is essential to the resistance against free radicals to minimize cell damages. Pretreating the cells with the present extract increases lactate production during the ischemic period, which apparently reflects the activation of a defense mechanism against the decrease in ATP provoked by ischemia. Kowalski 1992 and Groussard 2000 suggest that lactate could play a protective role in ischemia. Lactate could buffer superoxide (OH.), generating pyruvate which also buffers peroxide and superoxide, while decomposing into acetate and $CO_2$ (Herz 1997).

The potassium exit of a cell pre-treated with the present extract also supports a protective effect of the extract on a cell. Membrane component peroxidation may damage potassic channels (Halliwell 1999). The potassium release may be a beneficial adaptation against a metabolic stress (Wang et al. 1996). Potassium channel opening would permit capturing substrates for the intracellular ATP generation (Wondergem 1980). Potassium releasing would also inhibit $HCO_3^-$ transport, contributing to the acidification of the cytoplasm, which is also protective to the cell (Currin 1991). Potassium release appears early in a perfusate and precedes the ALT release, and is proportional to the ATP decrease (Mets 1993).

Sodium accumulation in the cell plays a major role in cell damage induced by I/R (Carini 2000, vanEchteld 1991 and Xia 1996). This increase may be due to: 1) a dysfunctional $Na^+/K^+$ pump, which is due to a decrease in ATP and to an increase of inorganic phosphate, or 2) a stimulation of the Na/H anti-carrier, due to the acidification of the cytoplasm (Zhao-fan 1996). Any reversal of such a situation could decrease the impact of a metabolic stress induced by sodium accumulation (Fiegen 1997). The sodium release may therefore be a defense mechanism against damages. Both decrease of potassium and sodium have been observed with livers perfused with present extract, which supports the protective effect of the extract in hepatic cells. Sodium release is superior in the treated group when compared to the control group, 10 minutes after re-perfusion, which suggests a late recovery in aTP contents in the controls.

The present extract stimulates the cellular mechanisms associated with cell protection against a radical attack.
The Ex-Vivo Effect of the Present Extract in Brain:

Numerous brain pathologies involve an increase production of free radicals. The latter are believed to contribute to the neurodegenerating process, namely pursuant to cerebral vascular accidents, or during the development of Alzheimer disease. It is believed that anti-radical components may be useful for reducing the expression of neurodegenerative diseases, or for their prevention or their treatment.

Hyppocampus region of the brain is vulnerable to neurotoxic effect of free radicals, namely during a cerebral anoxia. It has been demonstrated in vitro that neuronal transmission is attenuated during anoxia, because of the over expression of antioxidant molecules. Therefore, the effect of the present extract on the hyppocampal neuronal transmission was evaluated. Electrophysiological responses were registered in this brain structure. Particularly, the recovery of neuronal potentialisation would be studied. Hyppocampal slices of 450 μm thickness were obtained from rat brains and were transferred to electrophysiological chambers. The slices were maintained during 60 to 90 minutes in an oxygenated physiological solution, comprising or not different concentration or not different concentrations of the extract. After this resting period, electrical stimulation were applied every 25 seconds in hyppocampal afferences (Schaffer, regions of CA1 region). These electrical stimulations evolved synaptic responses. The initial slope of post-excitatory potentials was calculated to quantify the synaptic transmission efficacy pursuant anoxia. The study the neuronal potentialization, a high frequency stimulation train was applied to the neuronal circuits after anoxia. As a positive control, the response to glutamate with or without ischemia may be measured and the presence of the present extract should restore the response to glutamate.

Toxicity of FRTS/1

The toxicity has been evaluated in two different models: the in situ liver perfusion and in situ brain perfusion. These organs did not show any sign of toxicity due to the presence of the extract.

Adverse Reactions

The Present Extract is Non-Immunogenic.

The immune response provoked by the present extract has been evaluated by injecting 125 μg of the extract intraperitoneally in mice three times at 7 day intervals. After a week spent following the last injection, blood was harvested for immune serum obtention. The mice were anesthetized and the blood was taken by cardiac puncture. Blood samples were put immediately on ice. Blood clotting was allowed to proceed on ice and samples were centrifuged 12 hours after harvesting. The centrifuging conditions were the following: 10 minutes at 2500 g, which provided about 500 μl of serum. The extract was adsorbed on a microplate to provide a fixed antigen preparation. 200 μl of the extract (5 μl/ml) and 200 μl of ELISA buffer were poured in the wells of a 96-well plate. The ELISA buffer was made of 100 mM of sodium carbonate buffer (pH 9.6). After incubation of the antigen at 4° C. overnight, the non-adsorbed antigen was eliminated three washing steps with a sodium phosphate buffer 100 mM/NaCl, 100 mM (pH 7.4). The free adsorption sites were blocked in a 60 minute-incubation at room temperature with a solution of caseine 3% in the sodium phosphate/NaCl buffer. Excess of caseine was washed three times. The serum samples providing the antibodies, if any, were prepared as follows: serial dilutions in the sodium phosphate/NaCl buffer supplemented with 0.05% Tween 20™ were made and 25 μl of these dilutions were added to the wells. The microplate was further incubated for 1 h at 37° C., which step was followed by 5 washes with the sodium phosphate/NaCl/Tween buffer.

The presence of an antibody was revealed by the formation of an anti-Ig-peroxidase complex. 25 μl of the enzyme dilution in the sodium phosphate/NaCl/Tween buffer is added to each well followed by a one hour-incubation at 37° C. The enzyme dilution varied between 1:750 and 1-3000, depending on the conjugate (These are anti-Ig goat anti-sera, IgM, IgG, Ig1, Ig2 and Ig3, labelled with peroxidase). The labelling step was followed with 5 washings with the buffer. Substrate hydrogen peroxide 0.015% and the chromogene ABTS (2,2 azino-diethylbenzthiazoline-6-sulfonate) 0.05% dissolved in a phosphate citrate buffer 100 mM (pH 4.0) were added to the wells. Another 30 minute-incubation at room temperature and in the dark was allowed to proceed. The action of the enzyme released a colored substance which can be read spectrophotometrically at an absorbance wavelength of 405 nm. The serum level of antibody specific to the extract should be proportional to the color intensity. The results that have been obtained indicate that the extract is non-immunogenic to the recipient individuals.

These results indicate that the extract is not toxic to individuals, since it is neither hepatotoxic nor immunogenic.

Compositions and Dosage Regimens

Due to the stability and the potency of the present extract and the fact that it is non-toxic to animals, it is believed that dosage rates extending from 1 ng per kg of body weight to 1 g per kg of body weight per day could be administered to individuals in need for such administration (a dose in a lower μg range may be preferred). The dosage depends on the agressivity sought for the treatment of a disease. The dosages may also depend on the formulations and their route of administration. For example, a topical composition will not comprise the same dose as an intravenous composition or an enteral composition.

Topical Compositions for Treating Skin or Mucosal Diseases: Allergy/Asthma:

Brown Norway rats are high IgE producers. There is a well established model of allergen-induced airway hyperresponsiveness in Brown Norway rats[1] that reflects many features of human allergic asthma, including both early and late (70% of animals) phase reactions, increase in antigen-specific IgE following active immunization,[2] airway inflammations and increased bronchial responsiveness to several stimuli following allergen challenge.[4]

Measurement of Pulmonary Responses.

Brown Norway rats are sensitized by intraperitoneal injection of 1 ml of 1 mg ovalbumin/100 mg Al(OH)$_3$ in saline as previously described.[5] Twenty one days later, animals are anesthetized and intubated as previously described[6] with the end of the endotracheal tube connected to the Plexiglas box. A water-filled oesophageal catheter attached to a pressure transducer is used to determine changes in pleural pressure. Airflow is measured by a pneumotachograph coupled to a differential transducer attached to the Plexiglas box. Air flow, volume and transpulmonary pressure, pulmonary resistance ($R_L$) are determined at different times to identify both the early and late phase reactions. Sensitized Brown Norway rats are challenged with saline or ovalbumin (2% in saline) using the "Wright" nebuliser from Roxon Medi-Tech Lté (Montréal, PQ) using compressed air with a pressure giving an output of 0.1-0.2 ml/min passed into the Plexiglas box. Pulmonary resistance is measured every 5 minutes for the first hour and every 15 minutes for the next 10 hours. Pre-, co- and post-treatment with the extracts administered i.p. or by inhalation (about 1 to 100 μl) are tested in this model to provide improvement.

Protection Against UV Radiation

The ability of FRST/1 to prevent or reduce the UV-induced skin damages in hairless mice was investigated. As it is known that most of the skin cancers are induced by exposure to UV radiation, there is a need to identify new potent natural compounds that could prevent the adverse effects of UV radiation.

Animals

Hairless albino (SKH/1) mice will be purchased from Charles River laboratories (Wilmington, Mass.).

All mice are 6 weeks old at the beginning of the irradiation period. Mice are housed and maintained under standard conditions (23±10 C, 42±6% relative humidity, 12:12-h light-dark cycle) at the Animal Facility of IBS. Lights are automatically switched on daily at 7 AM and switched off daily at 7 PM. Mice are fed Purina chow diet (24% protein, 4% fat, and 4.5% fiber) and water ad libitum. For irradiation, mice are placed in plastic cages and are allowed to move freely within the cages during irradiation.

The animals were acclimated for one week prior to treatment and divided into randomly into 5 groups as follows.

Group I: Control non-irradiated, non-treated (n=5);
Group II: non-UV-irradiated animals treated with a preparation of topical ointment containing FRST/1 (n=5).
Groups III: UV irradiated animals treated with the preparation of topical ointment without FRST/1 (n=5)
Group IV: animals receiving topical application of the cream containing FRST/1 during UV irradiation (n=5).
Group V: non-treated UV-irradiated animals (n=5).

Treatments consist in:
1. Weighing all animals to assess their health on the day of the treatment and once every second day thereafter.
2. Performing a dorsal topical application of one type of cream (known to be non-toxic to animals and human). The cream contains or not FRST/1. The extract is present at a 1:10,000 dilution (starting from the lyophilized thylakoid fraction). One gram of cream is dispensed just before (and remain during and after UV irradiation) on the back of 3 groups of animals. Among these, one group of 5 animals receives the cream and no irradiation. One group receives the cream without FRST/1 and is exposed to UVB and one group receives the FRST/1 cream and UVB. The UVB irradiated groups (n=5) are exposed to sunlamps for 10 min once. One group (n=5) is exposed to UV sunlamps without cream treatment.
3. A single 10-min UVB irradiation by sunlamps located at 60 cm from the animal backs is performed. The two groups of 5 animals tested for cream protection (with and without FRST) and a single group of 5 animals without protection are submitted to the single dose of UVB.
4. After treatment, all animals are kept in cages and photographed from the top of the cage on the day of UV treatment and 3 to 4 days later, without manipulation.
5. After one week, the animals are sacrificed before removing a piece of their dorsal skin for further studies.

Westinghouse FS40 sunlamps, an IL-1400 radiometer, and a UVB photometer are used. The spectral irradiance for the UV lamps is 280-400 nm, 80% of which are in UVB region and 20% in WA region. The peak intensity of the light source are 297 nm. The fluence at 60 cm from the dorsal surface of the mice are 0.48-0.50 mJ/cm2/s. The mice are placed in plastic cages without lid as mentioned above.

Negative control mice (Groups I, II,) are treated in an identical way, but UV lamp is not be switched on. Group II receives the ointment without FRST/1 topically.

The mice from Group III, IV and V are given a single exposure of a total of 200 mJ UV light/cm 2 (acute dosage) for 10 min. In Group IV the animals receive topical application of a FRST/1 preparation immediately before, during and after UV exposure. This approach has been adopted to take into account minor differences in UV absorption characteristics (optical density differences) in the 290-320 nm range that might optically influence the UV light irradiation condition (Gonales and Pathak 1996).

The mice are kept and weighed every second day one week before and one week after UV irradiation. At the end of the experiment, the mice are sacrificed and the following parameters are compared in all the groups.

At the end of the experiment, the mice will be sacrificed and the following parameters will be compared in all the groups.
1. Body weight
2. Epidermal observation and photographs
3. Following sacrifice of the mice, a piece of the dorsal skin is surgically removed and used for further analyses.
4. Comparison of Cytokeratin patterns of expression by quantitative Western blot.

Solar radiation is the major environmental factor that affects the structure and function of human skin. Long term cutaneous photodamage as a consequence of cumulative UV radiation injury often leads to photoaging and skin cancer in fair-skinned individuals. Studies involving photobiological effects of ultraviolet radiation reveal that the ultraviolet B (UVB) component (290-320 nm) in particular is erythemogenic, carcinogenic and induces skin photoaging changes preceded by direct damage to DNA, RNA, proteins (including enzymes), cell membrane and other cell organelles; Tedesco, et. al. (1997).

Kligman and Kligman (1993) made a clear distinction between chronological aging and photoaging. Photoaging is used to describe the clinical and histological damages produced by chronic exposure of the skin to sunlight or solar-simulated UV radiation. Histologically, these changes are manifested in the form of marked changes in elasticity, glycosaminoglycans, and disordered collagen, together with an increase in the number of mast cells and inflammatory cells (Kligman and Gebre, 1991; Kaaresn and Poulsen, 1995; Poulsen et. al., 1984). This phenomenon of photoaging has clinically been recognized as irreversible, although recent therapeutic approaches have helped to minimize the over expression of intrinsic aging and photoaging changes (Gilchrest, 1996; Kang and Voorhees, 1998). The use of sunscreens on a regular basis has been reported to help prevent actinic damage to connective tissue (Snyder and May, 1975; Kligman and Kligman, 1982; Bissett et. al. 1991). The use of both sunscreens and antioxidants (e.g., green tea, Vitamin C, Vitamin E) appears to have an inhibitory effect on UVB-induced acute skin damage that contributes to both photoaging and photocarcinogenesis (Synder and May, 1975; Bissett et. al., 1991 and Huang et. al. 1997).

The photoprotective ability or antioxidant effect of FRST/1 against acute UV radiation exposure has been evaluated in the hairless albino mouse model.

The skin of hairless albino mouse (SKH-1) has been recognized as a useful and relevant experimental model for studying and understanding effects of UV radiation and photoaging of human skin (Kligman et. al., 1989; Bissett, et. al., 1987; Chatterjee et. al., 1990; Kligman and Gebre, 1991). The visually and microscopically recognizable responses of the epidermis and of the dermis to UVB radiation and absence of hair make the skin of hairless mice particularly useful in studying and evaluating the damaging effects of UV radiation. This mouse model has also been used to study and examine the immunological alterations and carcinogenesis induced by UVB radiation both locally in the skin and systematically (Fisher, et. al., 1989; Ho, et. al., 1992; Reeve, et. al., 1991).

Results:

Right after irradiation, all the non-treated irradiated mice showed signs of skin irritation and itchiness. They were otherwise healthy and active, although they did not gain weight. No symptoms of irritation or redness was observed on irradiated mice when pre-treated as well as when post-treated with FRST/1 and mice gained in weight in 80% of cases. Therefore, topical compositions, either solar screen lotion, cream, ointment, oil, gel or spray, are objects of this invention.

Skin Cytokeratins Analysis:

The cytokeratins 1 and 10 are representative of mature skin. A decrease in these keratins is an indication of epidermis regeneration following lesion.

The cytokeratins 5 and 8 are representatives of suprabasal and basal layers and are supposed to be expressed in actively proliferating epidermis.

The presence of these cytokeratins was evaluated with specific antibodies.

The extracts from mice skin were individually extracted and the skin of mice was analyzed individually per group. The same amount of total extracted cytoplasmic proteins was applied per well: 35 ug to enable comparison among animals and treatments.

Conclusions:

FRST/1 protected mice showed a pattern similar to that of controls untreated non-irradiated, while all other treatments showed a drastic decrease in high molecular weight keratins. Especially, cytokeratin 10 remained very well expressed in the skin of FRST/1 mice, which is a good indication of a protective effect. At a very low dose, the extract was active topically. The dose may be increased at will since the dose of the extract is not limited by any toxicity.

Although the present invention has been described hereinabove by way of preferred embodiments thereof, it can be modified, without departing from the spirit and nature of the subject invention as defined in the appended claims.

TABLE 1

Relative activity in function of the species and the exogen fluid

| Species | Relative Activity ±0.1 | Exogen fluid/ 67 g of plant ml |
|---|---|---|
| Spinacia oleracea | 1.12 | 193 |
| Common name: Spinach | 0.84 | 0 |
|  | 1.11 | 100 |
|  | 1.1 | 300 |
| Lycopersicon esculenta | 0.54 | 193 |
| Common name: Tomato |  |  |
| Capsicum annuum | 0.4 | 193 |
| Common name: Green pepper |  |  |
| Lactuca sativa Romaine | 0.83 | 193 |
| Common name: Romaine lettuce |  |  |
| Brassica oleracea capitata | 0.95 | 193 |
| Common name: Cabbage |  |  |
| Hordeum spp | 0.29 | 193 |
| Common name: Barley |  |  |
| Lactuca sativa (green ice) | 0.93 | 193 |
| Common name: Green ice lettuce |  |  |
| Lactuca sativa (Boston) | 0.97 | 193 |
| Common name: Boston lettuce | 0.8 | 0 |
|  | 1.5 | 100 |
|  | 0.95 | 300 |
| Crassula Arborescens | 0.71 | 193 |
|  | 0.02 | 0 |
|  | 0.37 | 100 |
|  | 0.67 | 300 |
| Picea mariana | 0.7 | 400 |
| Common name: Black Spruce |  |  |

BIBLIOGRAPHY

Eidelman, D. H., S. Bellofiore, and J. G. Martin. 1988. Late airway responses to antigen challenge in sensitized inbred rats. Am. Rev. Respir. Dis. 137:1033-1037.

Waserman, S., R. Olivenstein, P. M. Renzi, L. J. Xu, and J. G. Martin. 1992. The relationship between late asthmatic responses and antigen-specific immunoglobulin. J. Allergy Clin. Immunol. 90:661-669.

Renzi, P. M., R. Olivenstein, and J. G. Martin. 1993. Inflammatory cell populations in the airways and parenchyma after antigen challenge in the rat. Am. Rev. Respir. Dis. 147:967-974.

Bellofiore, S., and J. G. Martin. 1988. Antigen challenge of sensitized rats increases airway responsiveness to methacholine. J. Appl. Physiol. 65:1642-1646.

Elwood, W., J. O. Lötvall, P. J. Barnes, and K. F. Chung. 1991. Characterization of allergen-induced bronchial hyperresponsiveness and airway inflammation in actively sensitized Brown-Norway rats. J. Allergy Clin. Immunol. 88:951-960.

Renzi, P. M., J. P. Yang, T. Diamantstein, and J. C. Martin. 1996. Effects of depletion of cells bearing the interleukin-2 receptor on immunoglobulin production and allergic airway responses in the rat. Am. J. Respir. Crit. Care Med. 153:1214-1221.

Bailey S M, Reinke L A. Effect of low flow ischemia-reperfusion injury on liver function. Life Sci 66(11):1033-44, 2000.

Bruck R, Haddad P, Graf J, Boyer J L. Regulatory volume decrease stimulates bile flow, bile acid excretion, and exocytosis in isolated perfused rat liver. Am J Physiol 262: G806-12, 1992.

Caraceni P, Gasbarrini A, Van Thiel D H, Borle A B. Oxygen free radical formation by rat hepatocytes during postanoxic reoxygenation: scavenging effect of albumin. Am J Physiol 266:G451-8, 1994.

Carini R, De Cesaris M G, Splendore R, Bagnati M, Bellomo G, Albano E. Alteration of Na(+) homeostasis in hepatocytes reoxygenation injury. Biochem Biophys Acta 1500 (3):297-305, 2000.

Cohen A J, Burczynski F J, Rosser B G, Lipschitz J, Minuk G Y. The effects of various organ preservation solutions on hepatocyte membrane potentials, intracellular calcium concentrations, and outcome following liver transplantation. Am J Surg 179(2):154-60, 2000.

Currin R T, Gores G J, Thurman R G, Lemasters J J. Protection by acidotic pH against anoxic cell killing in perfused rat liver evidence for a pH paradox. FASEB J 5(2):207-10, 1991.

Drouin R, Milot M, Robert G, Massicotte D, Péronnet F, Lavoie C. Hepatic Glucagon Sensitivity Induced by Endurance Training: Effect mediated by Increased Glycogenolysis? MSSE: 32: S224 # 1061, 2000.

Erlinger S. Review article: new insights into the mechanisms of hepatic transport and bile secretion. J Gastroenterol Hepatol 11(6):575-9, 1996.

Fiegen R J, Rauen U, Hartman M, Decking U K, de Groot H. Decrease of ischemia injury to the isolated perfused rat liver by loop diuretics. Hepatology 25(6):1425-31, 1997.

Groussard C, Morel I, Chevanne M, Monnier M, Cillard J, Delamarche A. Free radical scavenging and antioxidant effects of lactate ion: an in vitro study. J Appl Physiol 89:169-175, 2000.

Halliwell B, Gutteridge J M. Free radicals in biology and medicine. Third edition, Oxford Science Publication, 1999.

Hashimoto K, Nishizaki T, Yoshizumi T, Uchiyama H, Okano S, Ikegami T, Yanaga K, Sugimachi K. Benfecial effect of FR167653 on colf ischemia/reperfusion injury in rat liver transplantation. Transplantation 70(9):1318-22, 2000.

Herz H, Blake D R, Grootveld M. Multicomponent investigations of the hydrogen peroxide- and hydroxyl radical-scavenging antioxidant capacities of biofluids: the role of exogenous pyruvate and lactate. Free Radic Res 26: 19-35, 1997.

Hwang K, Jeong D W, Lee J W, Kim I H, Chang H I, Kim H J, Kim I Y. Alteration of the NAD+/NADH ratio in CHO cells by stable transfection with human cytosolic glycerol-3-phosphate dehydrogenase: resistance to oxidative stress. Mol Cells 9(4):429-35, 1999.

Jaechke H. Glutathione disulfide as index of oxidant stress in rat liver during hypoxia. Am J Physiol 258(21):G499-G505, 1990.

Kowalski D P, Aw T Y, Park Y, Jones D P. Postanoxic oxidative injury in rat hepatocytes: lactate-dependent protection against tert-butylhydroperoxide. Free Radical Biol Med 12(3): 205-12, 1992.

Lavoie C, Drouin R., Milot M, Robert G, Massicotte D, Peronnet F. Hepatic Glucagon Sensitivity Induced by Endurance Training: Effect mediated by Increased Gluconeogenesis? MSEE 32: S224 # 1062, 2000

Lee S M, Park M J, Cho T S, Clemens M G. Hepatic injury and lipid peroxidation during ischemia and reperfusion. Shock 13(4):279-84, 2000.

Mallet R T, Hartman D A, Bunger R. Glucose requirement for postischemic recovery of perfused working heart. Eur J Biochem 188(2):481-93, 1990.

Peralta C, Bartrons R, Riera L, Manzano A, Xaus C, Gelpi E, Rosello-Catafau J. Hepatic preconditioning preserves energy metabolism during sustained ischemia. Am J Physiol Gastrointest Liver Physiol 279(1):G163-71, 2000.

Peralta C, Leon O S, Xaus C, Prats N, Jalil E C, Planell E S, Puig-Parellada P, Gelpi E, Rosello-Catafau J. Protective effect of ozone treatment on the injury associated with hepatic ischemia-reperfusion: antioxidant-prooxidant balance. Free Radical Res 31(3):191-6, 1999.

Ross B D. Perfusion techniques in biochemistry. Oxford University Press, Oxford, UK, 1972.

Saiki S, Yamaguchi K, Chijiiwa K, Shimizu S, Hamasaki N, Tanaka M. Phosphoenolpyruvate prevents the decline in hepatic ATP and energy charge after ischemia and reperfusion injury in rats. J Surg Res 73(1):59-65, 1997.

Sano W, Watanabe F, Tamai H, Furuya E, Mino E. Beneficial effect of fructose-1,6-bisphosphate on mitochondrial function during ischemia-reperfusion of rat liver. Gastroenterology 108(6):1785-92, 1995.

Smrekova R, Vajdova K, Kukan M, ulina O, Lutterova M, Wsolova L, Horecky J. A rapid, simple, and cost-effective method for screening liver preservation solutions in the rat. Transplantation 70(3):430-6, 2000.

Strubelt O, Younes M, Li Y. Protection by albumin against ischemia- and hypoxia-induced hepatic injury. Pharmacol Toxicol 75(5): 280-4, 1994.

Tamarina N Z, Chumakov V N, Lystsova G V. [Effect of NAD and ADP on glycolysis in the kidneys and liver of rats during ischemia]. WMJ 56(1):46-52, 1984.

van Echteld C J, Kirkels J H, Eijgelshoven M H, van der Meer P, Ruigrok T J. Intracellular sodium during ischemia and calcium-free perfusion: a 23Na NMR study. J Mol Cell Cardiol 23(3):297-307, 1991.

Vollmar B., Glasz J, Leiderer R, Post S, Menger M D. Hepatic microcirculatory perfusion failure is a determinant of liver dysfunction in warm ischemia-reperfusion. Am J Pathol 145(6):1421-31, 1994.

Wang Y, Sostman A, Roman R, Stribling S, Vignas S. Hannun Y, Raymond J, Fitz J G. Metabolic stress opens K(+) channels in hepatoma cells through a Ca(2+)— and protein kinase Cα-dependent mechanism. J Biol Chem 271(30): 18107-113, 1996.

Xia Z F, Horton J W, Zhao P Y, Babcock E E, Sherry A D, Malloy C R Effects of ischemia on intracellular sodium and phosphates in the in vivo rat liver. J Appl Physiol 81(3): 1395-403, 1996.

Youn Y K, Lalonde C, Demling R, Oxidants and the pathophysiology of burn and smoke inhalation injury, *Free Radic Biol Med,* 1992; 12(5):p. 409-15

Golan T D, Dan S, Haim H, Varda G, Sol K, Solar ultraviolet radiation induces enhanced accumulation of oxygen radicals in murine SLE-derived splenocytes in vitro, *Lupus* 1994; 3(2): p. 103-6

Lange R W, Germolec D R, Foley J F, Luster M I, Antioxidants attenuate anthralin-induced skin inflammation in BALB/c mice: role of specific proinflammatory cytokines. *J Leukoc Biol* 1998a; 64(2) p. 170-6

Lange R W, Hayden P J, Chignell C F, Luster M I, Anthralin stimulates keratinocyte-derived proinflammatory cytokines via generation of reactive oxygen species, *Inflamm Res* 1998b April; 47(4): p. 174-81.

Polla B S, Ezekowitz R A, Leung D Y, Monocytes from patients with atopic dermatitis are primed for superoxide production, *J Allergy Clin Immunol* 1992 89(2): p. 545-51

Juurlink B H, Paterson P G, Review of oxidative stress in brain and spinal cord injury: suggestions for pharmacological and nutritional management strategies, *J Spinal Cord Med* 1998; 21(4): p. 309-34

El Kossi M M, Zakhary M M, Oxidative stress in the context of acute cerebrovascular stroke, Stroke 2000; 31(8): p. 1889-92

Ebadi M, Srinivasan S K, Baxi M D, Oxidative stress and antioxidant therapy in Parkinson's disease, *Prog Neurobiol* 1996 January; 48(1) p. 1-19

Foler P. Riederer P. Influence of neurotoxins and oxidative stress on the onset and progression of Parkinson's disease. J Neurol. 2000 April; 247 Suppl 2:II82-94. Review.

Smith M A, Rottkamp C A, Nunomura A, Raina A K, Perry G, Oxidative stress in Alzheimer's disease, *Biochim Biophys Acta* 2000 Jul. 26; 1502(1): p. 139-44.

Cimen M Y, Cimen O B, Kacmaz M, Ozturk H S, Yorgacioglu R, Durak I. Oxidant/antioxidant status of the erythrocytes from patients with rheumatoid arthritis. Clin Rheumatol. 2000; 19(4):275-7.

Gerber R T, Holemans K, O'brien-Coker I, Mallet A I, Van Bree R, Van Assche F A, Poston L, Increase of the isoprostane 8-isoprostaglandin f2alpha in maternal and fetal blood of rats with streptozotocin-induced diabetes: evidence of lipid peroxidation. Am J Obstet Gynecol. 2000 October; 183(4):1035-40.

Sakorafas G H, Tsiotos G G, Sarr M G. Ischemia/Reperfusion-induced pancreatitis. Dig Surg. 2000; 17(1):3-14. Review.

McGuire G M, Liu P, Jaeschke H. Neutrophil-induced lung damage after hepatic ischemia and endotoxemia. Free Radic Biol Med. 1996; 20(2):189-97.

Lai H S, Chen W J, Chiang L Y. Free radical scavenging activity of fullerenol on the ischemia-reperfusion intestine in dogs. World J Surg. 2000 April; 24(4):450-4.

Eaton J W, UV-mediated cataractogenesis: a radical Perspective, *Doc Ophthalmol* 1994-95; 88(34): p. 233-42

Hardy P. Dumont I. Bhattacharya M. Hou X. Lachapelle P. Varma D R, Chemtob S. Oxidants, nitric oxide and prostanoids in the developing ocular vasculature: a basis for ischemic retinopathy. Cardiovasc Res. 2000 18; 47(3):489-509.

Castagne V, Clarke P G. Neuroprotective effects of a new glutathione peroxidase mimetic on neurons of the chick embryo's retina. J Neurosci Res. 2000 Feb. 15; 59(4):497-503

Singh R B, Singh N K, Rastogi S S, Wander G S, Aslam M, Onouchi Z, Kummerow F A, Nangia S. Antioxidant effects of lovastatin and vitamin E on experimental atherosclerosis in rabbits. Cardiovasc Drugs Ther. 1997; 11(4):575-80

Anastassopoulou J, Anifantakis B. Anifantakis Z A, Dovas A, Theophanides T. The role of free radical reactions with haemoglobin and thalassaemia. J Inorg Biochem. 2000; 79(14):327-9.

Ginsburg H. Golenser J. Redox metabolism in glucose-phosphate dehydrogenase deficient erythrocytes and its relation to antimalarial chemotherapy. Parassitologia. 1999 41(1-3):309-11.

Chen L Y, Nichols W W, Hendricks J, Mehta J L. Myocardial neutrophil infiltration, lipid peroxidation, and antioxidant activity after coronary artery thrombosis and thrombolysis. Am Heart J. 1995; 129(2):211-8

Montuschi P, Corradi M, Ciabatoni G, Nightingale J, Kharitonov S A, Barnes P J. Increased 8-isoprostane, a marker of oxidative stress, in exhaled condensate of asthma patients. Am J Respir Crit Care Med. 1999; 160(1):216-20

Montuschi P, Collins J V, Ciabattoni G, Lazzeri N, Corradi M, Kharitonov Sa, Barnes P J. Exhaled 8-isoprostane as an in vivo biomarker of lung oxidative stress in patients with COPD and healthy smokers. Am J Respir Crit Care Med. 2000; 162(3 Pt 1):1175-7

Barros L F, Stutzin A, Calixto A, Catalan M, Castro J, Hetz C, hermosilla Nonselective cation channels as effectors of free radical-induced rat liver cell necrosis. Hepatology. 2001; 33(1):114-122.

Jonas C R, Puckett A B, Jones D P, Griffith D P, Szeszycki E E, Bergman G F, Furr C E, Tyre C, Carlson J L, Galloway J R, Blumberg J B, Ziegler T R. Plasma antioxidant status after high-dose chemotherapy: a randomized trial of parenteral nutrition in bone marrow transplantation patients. Am J Clin Nutr. 2000; 72(1):181-9

El-Kadi A O, Bleau A M, Dumont I, Maurice H, du Souich P. Role of reactive oxygen intermediates in the decrease of hepatic cytochrome P450 activity by serum of humans and rabbits with an acute inflammatory reaction. Drug Metab Dispos. 2000; 28(9): 1112-20.

Prior R L, Prior R L, Cao G. Analysis of botanicals and dietary supplements for antioxidant capacity: a review. J AOAC Int. 2000; 83(4):950-6.

Lewen A, Matz P, Chan P H. Free radical pathways in CNS injury. J Neurotrauma. 2000; 17(10):871-90.

Sinha B K, Mimnaugh E G. Free radicals and anticancer drug resistance: oxygen free radicals in the mechanisms of drug cytotoxicity and resistance by certain tumors. Free Radic Biol Med. 1990; 8(6):567-81.

Karbownik M, Reiter R J, Garci J J, Tan D. Melatonin reduces phenylhydrazine-induced oxidative damage to cellular membranes: evidence for the involvement of iron. Int J Biochem Cell Biol. 2000; 32(10):1045-54.

Olszewski A J, McCully K S. Homocysteine metabolism and the oxidative modification of proteins and lipids. Free Radic Biol Med. 1993 June; 14(6):683-93.

Lieber C S. Ethanol metabolism, cirrhosis and alcoholism. Clin Chim Acta. 1997; 3; 257(1):59-84.

Cadenas E, Davies K J. Mitochondrial free radical generation, oxidative stress, and aging. Free Radic Biol Med. 2000; 29(3-4):222-30

Bednarska K, Wachowicz B, Buczynski A. UV-B-induced generation of free radicals in blood platelets. J Photochem Photobiol B. 2000; 55(2-3):109-12.

Floyd R A. Antioxidants, oxidative stress, and degenerative neurological disorders. Proc Soc Exp Biol Med. 1999; 222(3):236-45.

Blankenship R E, and Hartman H. The origin and evolution of oxygenic photosynthesis. Trends Biochem Sci. 1998, 23(3):94-97.

Allen M J & Crane A E. (1976). Null potential voltammetry—An approach to the study of plant photosystems. Bioelectrochem. Bioenerg. 3, 84-91.

Barber J. Kuhlbrandt W. Photosystem II. Curr. Opin Struct Biol. 1999, 9, 469-475.

Schlodder E, Witt H T, Stoichiometry of proton release from the catalytic center in photosynthetic water oxidation. Reexamination by a glass electrode study at ph 5.5-7.2. *J Biol Chem* 1999; 274 (43): 30387-92

Behera B K, and Misra B N. Analysis of the effect of industrial effluent on pigments, proteins, nucleic acids, and the 2,6-dichlorophenol indophenol Hill reaction of rice seedlings. Environ Res. 1983 August; 31(2):381-9.

Maxwell K. and Johnson G N. Chlorophyll fluorescence—a practical guide. J Exp Bot. 2000 April; 51(345):659-68. Review.

Furling D., Ghribi O., Lahsaini A. Mirault M E, Massicotte G. Impairment of synaptic transmission by transient hypoxia in hippocampal slices: improved recovery in glutathione peroxidase transgenic mice. Proc Natl Acad Sci U S A. 2000 11; 97(8):4351-6.

Engvall, E. (1980). Enzyme Immunoassay ELISA and EMIT. Methods in Enzymology 70, 419-439.

Starch M. J., Lohmann-Matthes, M. L. (1984). A new rapid method for Ig class and . . . J. Immunol. Methods 68, 304-309.

Claassen E, Kors, N., VanRooijen N. (1987). Immunology 60, 509-515.

The invention claimed is:

1. An extract from a photosynthetic organism obtainable by a method comprising:
   (a) providing a suspension of photosynthetic organism constituents that contain thylakoids;
   (b) disrupting the constituents while recovering thylakoids under light conditions which minimize light flux, in a medium comprising sugar or sugar alcohol and having a pH above 2 and below 10, the medium being added in a volume calculated upon the following equation:

(Volume of medium+organism constituents water content)/(Organism constituents dry weight)>10 to obtain a composition consisting essentially of thylakoids, cell debris/membranes and a liquid phase;
   (c) separating and isolating an extract from the cell debris/membranes and the liquid phase, wherein the separated and isolated extract consists essentially of pure stabilized integral thylakoids, the thylakoids comprising organized photosynthetic pigments in their fundamental state; and
   (d) eliminating any electron donor from the extract.

2. The extract according to claim 1, wherein the equation is:

(Volume of medium+organism constituents water content)/(Organism constituents dry weight)=25–150.

3. The extract according to claim 1, wherein the pH is between 5 and 8.

4. The extract according to claim 1, wherein the pH is between 6 and 7.5.

5. The extract of claim 1, wherein said organism is a plant.

6. The extract according to claim 5, wherein the suspension of step (a) is obtained by mechanically dispersing plant constituents or tissues in said medium.

7. The extract according to claim 5, wherein step (a) is preceded by a step of submitting a plant to a conditioning parameter selected from light, osmotic stress, heat, cold, freezing, dryness, hormones, chemical and biological inducers.

8. The extract according to claim 1, wherein step (a) is preceded by a step of conditioning said organism in a light environment of a wavelength comprised between about 500 and 600 nm, and step (b) is performed under the same light conditions.

9. The extract according to claim 1, wherein the medium comprises sorbitol in a concentration of about 0.2 to 1.5 M.

10. The extract according to claim 1, wherein the medium comprises sorbitol in a concentration of about 0.2 to 0.4 M.

11. The extract according to claim 1, wherein said medium comprises a buffer selected from a Tris buffer, an acetate buffer and an ascorbate buffer.

12. The extract according to claim 1, wherein said medium comprises about 20 mM Tris or acetate or ascorbate buffer having a pH of 7.5 and about 350 mM sorbitol or sucrose or fructose.

13. The extract according to claim 1, wherein the separation is based on a difference of sedimentation coefficient of each of the thylakoids, the cell debris/membranes, and the liquid phase.

14. The extract according to claim 13, wherein the separation comprises centrifugation in a tube equipped with a filter in a superior portion of the tube, the filter having a porosity onto which the cell debris/membranes deposit while the thylakoids and the liquid phase pass through the filter, the thylakoids forming a pellet in an inferior portion of the tube.

15. The extract according to claim 1, wherein water is eliminated by exchanging it against an amphoteric solvent or surfactant after step (c).

16. The extract according to claim 15, wherein water is eliminated by exchanging it against propylene glycol.

17. The extract according to claim 1 that is in a state selected from a dry state, a partly or totally solubilized state, and a suspension.

18. A composition comprising the extract according to claim 1.

* * * * *